United States Patent
Tsubouchi et al.

(10) Patent No.: US 9,272,018 B2
(45) Date of Patent: Mar. 1, 2016

(54) ACUTE HEPATIC INSUFFICIENCY DEPRESSANT AND METHOD FOR EVALUATING DRUG EFFICACY THEREOF

(75) Inventors: Hirohito Tsubouchi, Kyoto (JP); Akio Ido, Kyoto (JP); Tsutomu Chiba, Kyoto (JP); Akira Shimizu, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 14/112,490

(22) PCT Filed: Apr. 18, 2012

(86) PCT No.: PCT/JP2012/060505
§ 371 (c)(1),
(2), (4) Date: Jan. 7, 2014

(87) PCT Pub. No.: WO2012/144535
PCT Pub. Date: Oct. 26, 2012

(65) Prior Publication Data
US 2014/0234341 A1    Aug. 21, 2014

(30) Foreign Application Priority Data

Apr. 18, 2011    (JP) .................. 2011-092516

(51) Int. Cl.
*A61K 38/18* (2006.01)
*C07K 14/475* (2006.01)
*A61K 39/395* (2006.01)
*G01N 33/68* (2006.01)

(52) U.S. Cl.
CPC ......... *A61K 38/1833* (2013.01); *A61K 39/3955* (2013.01); *C07K 14/4753* (2013.01); *G01N 33/6893* (2013.01); *G01N 2800/085* (2013.01); *G01N 2800/52* (2013.01)

(58) Field of Classification Search
None
See application file for complete search history.

(56) References Cited

U.S. PATENT DOCUMENTS 5,500,354 A    3/1996    Kitamura et al.

FOREIGN PATENT DOCUMENTS

| JP | H03-086835 A | 4/1991 |
| JP | 2577091 B2 | 1/1997 |
| JP | H10-167982 A | 6/1998 |

OTHER PUBLICATIONS

Ido et al.: Safety and pharmacokinetics of recombinant human hepatocyte growth factor (rh-HGF) in patients with fulminant hepatitis: a phase I/II clinical trial, following preclinical studies to ensure safety. Journal of Translational Medicine 2011 9:55.*
Hasuike et al., *Journal of Gastroenterology and Hepatology*, 20: 1753-1761 (2005).
Ido et al., *Journal of Abdominal Emergency Medicine*, 29(4): 609-611 (2009).
Ido et al., *Journal of Gastroenterology*, 101 (special extra issue Taikai): A222, entry S3-9 (2004).
Ishii et al., *Journal of Biochemistry*, 117: 1105-1112 (1995).
Kosai et al., *Biochemical and Biophysical Research Communications*, 244: 683-690 (1998).
Kosai et al, *Hepatology*, 30: 151-159 (1999).
Okano et al., *Hepatology*, 26: 1241-1249 (1997).
Shiota et al., *Res. Commun. Mol. Pathol. Pharmacol.*, 101(1): 3-12 (1998).
Taketa, Kazuhisa, *Hepatology*, 12: 1420-1432 (1990).

* cited by examiner

*Primary Examiner* — Marianne P Allen
(74) *Attorney, Agent, or Firm* — Leydig, Voit & Mayer, Ltd.

(57) ABSTRACT

The present invention provides a therapeutic agent for acute liver failure containing a hepatocyte growth factor (HGF), particularly an agent for treating fulminant hepatitis or late onset hepatic failure or suppression of progression of acute liver failure without hepatic coma to fulminant hepatitis or late onset hepatic failure. The present invention also provides a method for evaluating the efficacy of HGF including measuring the amount of α-fetoprotein (liver regeneration biomarker) and/or soluble Fas (anti-apoptotic biomarker) in a sample obtained from a liver injury patient administered with HGF.

12 Claims, 10 Drawing Sheets ic. Moreover, whether AFP value and/or soluble Fas value
ACUTE HEPATIC INSUFFICIENCY DEPRESSANT AND METHOD FOR EVALUATING DRUG EFFICACY THEREOF

CROSS-REFERENCE TO RELATED APPLICATIONS

This patent application is the U.S. national phase of International Patent Application No. PCT/JP2012/060505, filed Apr. 18, 2012, which claims the benefit of Japanese Patent Application No. 2011/092516, filed on Apr. 18, 2011, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 17,098 bytes ASCII (Text) file named "714434SequenceListing.txt," created Oct. 17, 2013.

TECHNICAL FIELD

The present invention relates to a therapeutic agent for acute liver failure and a method for evaluating the drug efficacy thereof. More specifically, the present invention relates to an acute liver failure suppressing agent containing a hepatocyte growth factor (HGF), particularly a prophylactic and/or therapeutic agent for fulminant hepatitis and late onset hepatic failure, and a method for evaluating the drug efficacy of human HGF, comprising measuring the amount of α-fetoprotein and/or soluble Fas in the body of a hepatic failure patient who underwent a treatment with HGF, and the like.

BACKGROUND ART

Acute liver failure (ALF) is a fatal clinical syndrome characterized by an abrupt loss of hepatocellular function, which causes coagulopathy, jaundice and encephalopathy. In our country, acute liver failure with a histological appearance of hepatitis is classified as fulminant hepatitis (FH) or late-onset hepatic failure (LOHF). Fulminant hepatitis is a disease with extremely poor prognosis, for which liver transplantation has solely been established as a treatment method that improves the lifesaving rate thereof. Due to the donor shortage and the like, however, the executing rate thereof is only just over 20%, and the lifesaving rate by a medical treatment is as low as 20-50%. Therefore, it is an urgent task to develop a new treatment method with verified effectiveness.

Hepatocyte growth factor (HGF) is a growth factor having a potent promoting effect on liver regeneration, which is isolated from the plasma of patients with fulminant hepatitis (e.g., see patent document 1). Since HGF has been found to have, in addition to a hepatocyte proliferative or regenerative action (e.g., see non-patent documents 1 and 2), a wide variety of physiological activities such as a hepatocyte-protective action (e.g., see non-patent documents 3-5) by anti-apoptosis, an anti-fibrotic action and the like, a treatment of hepatic failure by HGF is expected. Although the effectiveness has been confirmed in vitro and in animal models, the efficacy, safety and the like of HGF in the human body are still unclear. Particularly, the lifesaving effect in acute liver failure with extremely poor prognosis such as fulminant hepatitis and late onset hepatic failure, and whether HGF administration is effective for the prevention of acute liver failure associated with encephalopathy without coma from becoming fulminant cannot be predicted at all. In addition, a possibility of HGF administration causing side effects such as decreased blood pressures, renal toxicity and the like was suggested in pre-clinical safety tests. However, an administration protocol that avoids those side effects in clinical situations has not been established.

Moreover, a technique and an index for monitoring the efficacy of HGF, i.e., liver regeneration promoting action and anti-apoptotic action, in the human body have not been developed heretofore. In the animal experiment level, the liver regeneration promoting action of the recombinant human HGF has been appreciated in view of the increased liver weight and increased serum albumin value thereby (non-patent document 6). However, the evaluation based on an increase in the liver weight (liver volume) cannot provide a real-time evaluation of liver regeneration induction, since the time necessary for increasing the weight (volume) after the induction of liver regeneration is long. Moreover, the serum albumin value reflects improved liver synthesizability as the result of liver regeneration, and is not suitable as an index for liver regeneration per se.

α-Fetoprotein (AFP) is a glycoprotein with a molecular weight of 67 kDa, which is found in the human fetal serum, and is practically used as a serum immunological diagnosis marker for hepatocellular carcinoma. In animal disease models, AFP is expressed in immature hepatocytes such as liver progenitor cell, hepatoblast and the like, and clinically, it has been reported that the serum AFP value reflects liver regeneration and mildly increases in fulminant hepatitis and chronic hepatitis (non-patent document 7).

On the other hand, soluble Fas is a Fas present on a cell surface, which is cleaved and released into the blood, and binds to Fas ligand to antagonize the binding of Fas and Fas ligand on the cell surface, thus suppressing apoptosis.

In fulminant hepatitis, the blood HGF value important for the prediction of prognosis remarkably increases. However, since a correlation is not found between blood HGF value, and serum AFP value and soluble Fas value, there was no prediction on the utilizability of AFP and soluble Fas as an index (efficacy biomarker) for the treatment effect of exogenous HGF administration.

DOCUMENT LIST

Patent Document patent document 1: JP-B-2577091

Non-Patent Documents non-patent document 1: Ishii, T. et al., J. Biochem., 117: 1105-1112 (1995)
non-patent document 2: Hasuike, S. et al., J. Gastroenterol. Hepatol., 20: 1753-1761 (2005)
non-patent document 3: Okano, J. et al., Hepatology, 26: 1241-1249 (1997)
non-patent document 4: Kosai, K. et al., Biochem. Biophys. Res. Commun., 244: 683-690 (1998)
non-patent document 5: Kosai, K. et al., Hepatology, 30: 151-159 (1999)
non-patent document 6: Ishii, T. et al., J. Biochem., 117: 1105-1112 (1995)
non-patent document 7: Taketa, K., Hepatology, 12: 1420-1432 (1990)

SUMMARY OF THE INVENTION

Problems to be Solved by the Invention

An object of the present invention is to provide an effective and safe therapeutic means for acute liver failure other than liver transplantation, and an evaluation means of the treatment effect.

Means of Solving the Problems

In an attempt to achieve the aforementioned object, the present inventors have conducted phase I/II investigator-initiated clinical trials of recombinant human HGF (rh-HGF) in fulminant hepatitis and late onset hepatic failure patients, capable of receiving liver transplantation, as subjects. To be specific, rh-HGF was repeatedly administered to the patients, the pharmacokinetics and life-prolonging effect thereof, and expression of the side effects predicted from the preclinical safety tests were verified, as well as a search of an efficacy biomarker capable of highly sensitively and highly accurately monitoring the treatment effect of rh-HGF was conducted. As a result, it was found that rh-HGF is effective for the treatment of acute liver failure with hepatic encephalopathy, such as fulminant hepatitis, late onset hepatic failure and the like, and prevention of acute liver failure without hepatic coma from being fulminant. It was also unexpectedly found that the levels of α-fetoprotein (AFP) and soluble Fas in the serum increase in good correlation with an increase in the blood HGF concentration due to rh-HGF administration. Thus, they have successfully identified AFP and soluble Fas as biomarkers capable of real-time monitoring of a hepatocyte regenerative action and an anti-apoptotic (hepatocyte protection) action in rh-HGF treatments. They have also confirmed that the administration protocol revised to be suitable for avoiding the side effects such as a decrease in the blood pressure, renal toxicity and the like in the preclinical test is also clinically effective. The present inventors have conducted further studies based on these findings, and completed the present invention.

Accordingly, the present invention provides the following.

[1] An acute liver failure suppressing agent, comprising a hepatocyte growth factor.

[2] The agent according to [1] for the treatment of fulminant hepatitis or late onset hepatic failure, or suppression of the progression from acute liver failure without hepatic coma to fulminant hepatitis or late onset hepatic failure.

[3] The agent according to [1] or [2], which is systemically administered while stepwisely or continuously increasing the administration rate in a single administration.

[4] The agent according to [3], which is intravenously administered by about 10% of one dose in the first ⅓ of the single administration time, about 30% of one dose in the next ⅓ of the single administration time, and about 60% of one dose in the final ⅓ of the single administration time.

[5] The agent according to any of [1] to [4], wherein the hepatocyte growth factor is derived from human.

[6] A method for evaluating the efficacy of a hepatocyte growth factor, comprising measuring the amount of α-fetoprotein and/or soluble Fas in a sample collected from a liver injury patient administered with the hepatocyte growth factor.

[7] The method according to [6], wherein the α-fetoprotein is an index of liver regenerative effect and the soluble Fas is an index of anti-apoptotic effect.

[8] The method according to [6] or [7], comprising comparing the measurement value of the α-fetoprotein and/or soluble Fas with that in a sample collected from the patient before administration of the hepatocyte growth factor and, when the amount of the α-fetoprotein and/or soluble Fas increased from that before the administration, judging that the hepatocyte growth factor has a treatment effect.

[9] The method according to any of [6] to [8], comprising monitoring the amount of the α-fetoprotein and/or soluble Fas in the sample collected from the patient over time during the administration period of the hepatocyte growth factor and, when the amount of the α-fetoprotein and/or soluble Fas increased in the administration period, judging that the hepatocyte growth factor has a treatment effect.

[10] The method according to any of [6] to [9], wherein the sample is serum or plasma.

[11] The method according to any of [6] to [10], wherein the patient is an acute liver failure patient.

[12] The method according to [11], wherein the patient is a patient with fulminant hepatitis or late onset hepatic failure, or a patient with acute liver failure without hepatic coma.

[13] The method according to any of [6] to [12], wherein the patient is not administered with a steroid-based anti-inflammatory agent when α-fetoprotein is used as an index.

[14] The agent according to any of [1] to [5], wherein the dose is increased and/or the administration period is extended when the efficacy of the human hepatocyte growth factor is not found by the method according to any of [6] to [13].

[15] A kit for efficacy evaluation of a human hepatocyte growth factor, comprising an anti-α-fetoprotein antibody and/or an anti-soluble Fas antibody.

[16] The agent according to any of [1] to [5], which is combined with the kit of [15].

Effect of the Invention

Human HGF is useful for preventing acute liver failure patients who cannot receive liver transplantation, particularly patients with acute liver failure without hepatic coma before progression to fulminant hepatitis or late onset hepatic failure, from being fulminant, since it shows a constant lifesaving effect even for acute liver failure with extremely poor prognosis, such as fulminant hepatitis, late onset hepatic failure and the like. Since AFP and soluble Fas respectively reflect sharply a liver regenerative effect and an anti-apoptotic (hepatoprotection) effect afforded by the administration of human HGF, a real-time judgment of whether the administration of human HGF can provide the expected efficacy is possible, based on which the dose and/or the administration period of human HGF can be optimized (stratified).

BRIEF DESCRIPTION OF THE DRAWINGS

FIG. 7-1 shows clinical course of patient with subacute fulminant hepatitis (FHSA) caused by hepatitis E virus infection (67 years old, Japanese male; patient 1). On admission, he presented with hepatic encephalopathy, jaundice, ascites, edema, and microhematuria caused by bladder catheter. Although ALT had already decreased to 32 IU/L, thrombocytopenia ($6.1 \times 10^4$/µL), increased T-Bil (11.2 mg/dL), a marked decrease in serum albumin (2.9 g/dL), and prolonged PT (33%) (PT-INR 2.07) were observed, suggesting that hepatic functional reserve was markedly impaired. Serum HGF and AFP levels were 0.77 and 7.0 ng/mL, respectively, and liver volume measured by CT was 1055 mL. Following observation of general condition for 2 days, administration of rh-HGF (0.6 mg/m$^2$/day) was initiated. Because of an increase in serum creatinine level of 2.0 mg/dL, caused by diuretics administration to reduce massive ascites, protocol therapy was discontinued on day 14, resulting in 13-day administration of rh-HGF. Although prolonged PT was stable during rh-HGF administration and observation period, T-Bil gradually increased and hepatic encephalopathy did not improve. Hepatic failure gradually progressed after the observation period. The patient ultimately died 68 days after the onset of hepatic encephalopathy. In the Figure, PE shows plasma exchange and CHDF shows performance of continuous hemodiafiltration.

FIG. 7-2 shows clinical course of patient with FHSA of undetermined etiology (71 years old, Japanese female; patient 2). She presented with mild hepatic encephalopathy with flapping tremor, jaundice, and urinary findings, including proteinuria and microhematuria, caused by bladder catheter. Platelet count and serum albumin level decreased to $6.9 \times 10^4$ µL, and 3.2 g/dL, respectively, and PT was prolonged to 49% (PT-INR 1.55). In addition to increased T-Bil level of 6.9 mg/dL, serum ALT level increased to 131 IU/L. Serum HGF and AFP levels were 1.94 and 22.9 ng/mL, respectively, and liver volume was 595 mL. Following observation of general condition for 24 hours, treatment with rh-HGF was initiated, and the protocol therapy was continued for 14 days without any severe adverse events. Hepatic encephalopathy disappeared after plasma exchange (PE) on day 2. Consciousness level was not impaired throughout the study period. Although intravenous administration of rh-HGF reduced systolic blood pressure, the patient maintained lucidity and did not complain any symptom. Although prednisolone (PSL) was administered to reduce ALT, blood biochemical findings and patient condition were stable throughout the study period. After the completion of the study, biochemical findings were gradually improved, and, finally, the patient survived.

FIG. 7-3 shows clinical course of patient with late onset hepatic failure (LOHF) of undetermined etiology (64 years old, Japanese female; patient 3). The patient accompanied advanced hepatic encephalopathy (HE) and showed platelet count: $9.2 \times 10^4$/µL, PT: 37% (PT-INR: 1.78), T-Bil level: 11.7 mg/dL, ALT level: 260 IU/L, and serum albumin level: 2.9 g/dL. Serum HGF and AFP levels were 1.07 and 3.9 ng/mL, respectively, and liver volume was 640 mL. Because of oliguria (392 mL/day), protocol therapy was discontinued on day 13, resulting in 12-day administration of rh-HGF. Serum ALT levels reduced immediately, and hepatic encephalopathy was transiently improved during rh-HGF administration period. However, hepatic encephalopathy, prolonged PT, and an increase in T-Bil progressed during the observation period, and the patient died during the observation period (28 days after the onset of hepatic encephalopathy).

FIG. 7-4 shows clinical course of patient with FHSA caused by a supplement containing coenzyme Q-10 (40 years old, Japanese male; patient 4). The patient showed decrease of platelet count ($7.0 \times 10^4$/µL), PT: 43% (PT-INR 1.62), T-Bil level: 27.6 mg/dL, ALT level: 253 IU/L and serum albumin level: 2.9 g/dL, but did not show hepatic encephalopathy (HE) (which was temporarily observed before enrollment). Serum HGF and AFP levels were 1.88 and 39.7 ng/mL, respectively, and liver volume was 1110 mL. Administration of rh-HGF was continued for 14 days, and PSL was administered to reduce ALT throughout the study period. An increase in T-Bil and prolonged PT was modestly improved during rh-HGF administration, followed by further improvement after the observation period. Ultimately, the patient survived.

DESCRIPTION OF EMBODIMENTS

Figure 1:
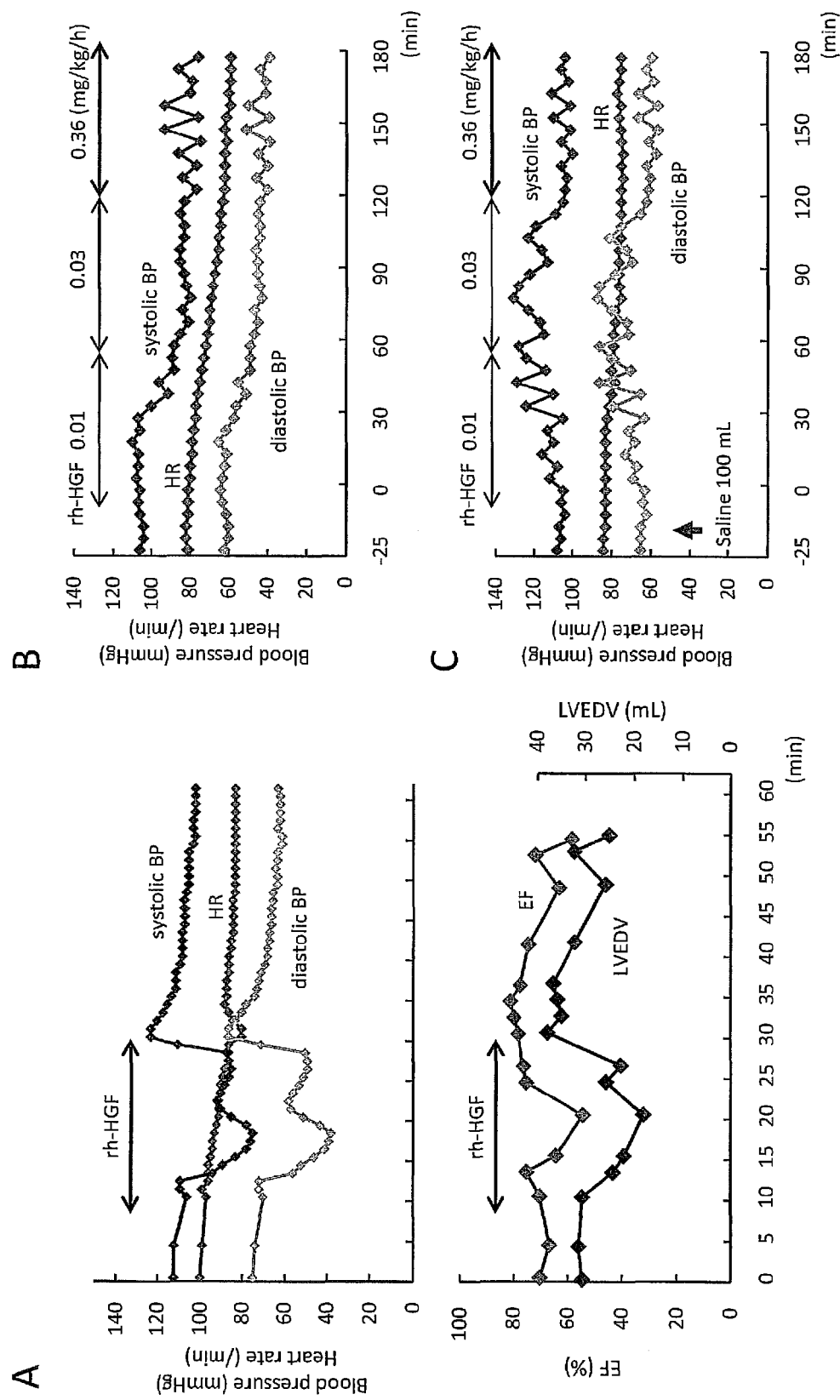
FIG. 1 shows that intravenous injection of rh-HGF lowers the blood pressure through capacitance vessels in miniature swine. The effects of intravenously administered rh-HGF on the systolic blood pressure (systolic BP), diastolic blood pressure (diastolic BP), heart rate (HR), and cardiac function was examined in miniature swine under general anesthesia. (A) Intravenous injection of rh-HGF (1.0 mg/kg) rapidly reduced systolic and diastolic blood pressure. Reduced blood pressure was persistent during rh-HGF administration (for 20 min), and was immediately recovered after the completion of rh-HGF injection (upper panel). Echocardiography showed that ejection fraction (EF) and left ventricular end-diastolic volume (LVEDV) were reduced during rh-HGF administration. (B) Administration of rh-HGF (0.4 mg/kg) while increasing the administration rate stepwisely over 3 hr (0.01 mg/kg for the first 60 min, 0.03 mg/kg for the next 60 min, and 0.36 mg/kg for the last 60 min) gradually decreased the blood pressure and heart rate. (C) Infusion of 100 mL of saline prior to rh-HGF administration enabled prevention of a decrease in BP during rh-HGF administration.

Human hepatocyte growth factor (HGF), which is the active ingredient of the acute liver failure suppressing agent of the present invention, is not particularly limited as to its derivation as long as it is a protein containing an amino acid sequence the same as or substantially the same as the amino acid sequence shown by amino acid Nos. 30-728 or 32-728 in the amino acid sequence shown by SEQ ID NO: 2, and may be a protein derived from a cell of human or other warm-blooded animal (e.g., bovine, swine, mouse, rat, hamster, monkey, horse, sheep, goat, rabbit, guinea pig, chicken and the like) [for example, hepatocyte, splenocyte, renal tubule cell, keratinocyte, vascular endothelial cell, myelocyte, mesangial cell, nerve cell, glial cell, pancreatic β cell, Langerhans' cell, epidermal cell, epithelial cell, goblet cell, smooth muscle cell, skeletal muscle cell, fibroblast, fibrocyte, adipocyte, immunocyte, megakaryocyte, synovial cell, chondrocyte, bone cell, osteoblast, osteoclast, mammary gland cell, interstitial cell, or a corresponding progenitor cell, stem cell, establish or cancer cell thereof, and the like] or any tissue or organ containing such cell [for example, liver, spleen, placenta, urinary duct, kidney, blood vessel, skin, bone marrow, spinal cord, hypophysis, stomach, pancreas, gonad, thyroid, gallbladder, adrenal gland, muscle (skeletal muscle, smooth muscle), lung, gastrointestinal tract (e.g., large intestine and small intestine), heart, thymus, submandibular gland, peripheral blood, prostate, testicle, ovary, uterus, bone, joint, adipose tissue (e.g., brown adipose tissue, white adipose tissue), and the like], or a protein synthesized chemically or biochemically using a cell-free protein synthesis system. Preferably, it is a recombinant protein produced from a transformed cell introduced with a nucleic acid containing a nucleotide sequence encoding the above-mentioned amino acid sequence.

The amino acid sequence substantially the same as the amino acid sequence shown by amino acid Nos. 30-728 or 32-728 in the amino acid sequence shown by SEQ ID NO: 2 is an amino acid sequence having not less than about 90%, preferably not less than about 95%, more preferably not less than about 97%, particularly preferably not less than about 98%, identity with the amino acid sequence shown by amino acid Nos. 30-728 or 32-728 in the amino acid sequence shown by SEQ ID NO: 2, where a protein containing the amino acid sequence shows substantially the same quality of activity as a protein containing the amino acid sequence shown by SEQ ID NO: 2.

The identity of the amino acid sequences in the present specification can be calculated under the following conditions (an expectation value=10; gaps are allowed; matrix=BLOSUM62; filtering =OFF) using a homology scoring algorithm NCBI BLAST (National Center for Biotechnology Information Basic Local Alignment Search Tool).

Examples of substantially the same quality of activity include hepatoprotective (apoptosis suppressive) action, liver regeneration promoting action and the like. Being "substantially the same quality" means that the activities thereof are qualitatively (e.g., physiologically or pharmacologically) the same. Therefore, while the activities such as apoptosis suppressive action, liver regeneration promoting action and the like are preferably equivalent (e.g., about 0.5- to about 2-fold), quantitative factors such as the level of these activities, the molecular weight of the proteins and the like may be different.

HGF to be used in the present invention is preferably human HGF (pro-HGF) having the amino acid sequence shown by amino acid Nos. 30-728 or 32-728 in the amino acid sequence shown by SEQ ID NO: 2, an ortholog thereof in other mammal, natural allele variant or polymorphic variant in human HGF, or a splice variant thereof.

HGF is biosynthesized as a single strand protein (pro-HGF) having an intramolecular disulfide bond, and thereafter cleaved by HGF activator to become biologically active mature HGF with a double stranded structure. HGF to be used in the present invention may be any of a pro type and a mature protein, and pro-HGF having a single strand is preferably used.

HGF may be a free form or a salt form. Examples of the salt of HGF include physiologically acceptable salts with acid (e.g., inorganic acid, organic acid) and base (e.g., alkali metal), with particular preference given to physiologically acceptable acid addition salts. Such salts include, for example, salts with inorganic acids (e.g., hydrochloric acid, phosphoric acid, hydrobromic acid, sulfuric acid), or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

HGF can be isolated and purified from a cell or tissue that naturally produces the same or a primary culture thereof or an established line of the cell, for example, patient plasma obtained by a plasma exchange method as a treatment of fulminant hepatitis and the like, by a method combining protein purification techniques known per se, for example, several kinds of column chromatographies as in the method described in J. Clin. Invest., 81: 414 (1998).

HGF can also be produced by a publicly known method of peptide synthesis. The method of peptide synthesis may be any of, for example, a solid phase synthesis process and a liquid phase synthesis process. That is, a desired protein can be produced by condensing a partial peptide or amino acids capable of constituting the HGF and the remaining portion, and eliminating any protecting group the resultant product may have. Here, condensation and elimination of the protecting group are performed according to a method known per se, for example, the method described in (1) or (2) below.

(1) M. Bodanszky and M. A. Ondetti, Peptide Synthesis, Interscience Publishers, New York (1966)
(2) Schroeder and Luebke, The Peptide, Academic Press, New York(1965)

Thus-obtained protein can be purified and isolated by a known purification method. Examples of the purification method include solvent extraction, distillation, column chromatography, liquid chromatography, recrystallization and a combination of these. When the protein obtained by the method is a free form, the free form can be converted to an appropriate salt by a publicly known method or a method based thereon; conversely, when the protein is obtained in the form of a salt, the salt can be converted to a free form or another salt by a publicly known method or a method based thereon.

Moreover, an HGF can also be produced by culturing a transformant having the nucleic acid encoding same, and separating and purifying a recombinant HGF from the obtained culture. The nucleic acid that encodes HGF may be DNA or RNA, or a DNA/RNA chimera, and is preferably DNA. In addition, the nucleic acid may be a double-strand, or single-strand. The double-strand may be a double-stranded DNA, a double-stranded RNA, or a DNA:RNA hybrid, preferably a double-strand DNA.

Examples of the DNA encoding HGF include genomic DNA, cDNA (cRNA) derived from a cell of human or other warm-blooded animal that produces HGF, or any tissue or organ containing such cell, synthetic DNA (RNA) and the like. The genomic DNA and cDNA encoding HGF can also be directly amplified by Polymerase Chain Reaction (PCR) method and Reverse Transcriptase-PCR (RT-PCR) method using the genomic DNA fraction and total RNA or mRNA fraction prepared from the above-mentioned cells or tissues each as a template. Alternatively, genomic DNA and cDNA encoding HGF can also be cloned by colony or plaque hybridization method, PCR method and the like, from the genomic DNA library or cDNA library (preferably cDNA library derived from liver, spleen or placenta) prepared by inserting, into a suitable vector, a frayment of genomic DNA and total RNA or mRNA prepared from the above-mentioned cell/tissue. The vector to be used for the library may be any of bacteriophage, plasmid, cosmid, phagemid and the like.

Examples of the nucleic acid encoding HGF include a nucleic acid containing the nucleotide sequence shown by SEQ ID NO: 1, a nucleic acid containing a nucleotide sequence capable of hybridizing with a sequence of complementary strand to the nucleotide sequence shown by SEQ ID NO: 1 under stringent conditions, and encoding a protein having substantially the same quality of activity [e.g., apoptosis suppressive action, liver regeneration promoting action and the like] as that of HGF, as mentioned above, and the like.

As the nucleic acid capable of hybridizing with a sequence of complementary strand to the nucleotide sequence shown by SEQ ID NO: 1 under stringent conditions, a nucleic acid containing a base sequence having not less than about 85%, preferably not less than about 90%, more preferably not less than about 95%, particularly preferably not less than about 97%, identity with the nucleotide sequence shown by SEQ ID NO: 1 and the like are used.

The identity of the base sequences in the present specification can be calculated under the following conditions (expectation value=10; gaps are allowed; filtering=ON; match score=1; mismatch score=−3) using a homology scoring algorithm NCBI BLAST (National Center for Biotechnology Information Basic Local Alignment Search Tool).

The hybridization can be performed by a method known per se or a method analogous thereto, for example, a method described in Molecular Cloning, 2nd ed. (J. Sambrook et al., Cold Spring Harbor Lab. Press, 1989) and the like. When a commercially available library is used, hybridization can be performed according to the method of the attached manufacturer's protocol. Hybridization can be preferably performed under high stringent conditions. Examples of the high stringent conditions include reaction conditions characterized by (1) low ionic strength and high temperature for washing, for example, 0.015 M sodium chloride/0.0015 M sodium citrate/0.1% sodium dodecyl sulfate is used at 50° C., and (2) denaturant such as formamide, for example, 0.1% bovine serum albumin/0.1% ficoll/0.1% polyvinylpyrrolidone/50 mM sodium phosphate buffer (pH 6.5) with 750 mM sodium chloride, 75 mM sodium citrate, and 50% (v/v) formamide are used together at 42° C. Alternatively, the stringent conditions may include use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated sermon sperm DNA (50 μg/ml), 0.1% SDS, and 10% dextran sulfate at 42° C., washing with 0.2×SSC and 50% formaldehyde at 55° C., followed by high stringent washing with 0.1×SSC containing EDTA at 55° C. Those of ordinary skill in the art can easily realize desired stringency by appropriately controlling temperature of hybridization reaction and/or washing, ionic strength of buffer and the like, in consideration of the factors such as probe length and the like.

The nucleic acid encoding HGF to be used in the present invention is preferably human prepro-HGF having the nucleotide sequence shown by SEQ ID NO: 1, an ortholog thereof in other mammal, natural allele variant or polymorphic variant in human prepro-HGF, or a splice variant thereof.

The base sequence of the DNA can be converted according to a method known per se, such as the ODA-LA PCR method, the Gapped duplex method, or the Kunkel method, or a method based thereon, using a commonly known kit, for example, Mutan™-super Express Km (TAKARA SHUZO CO. LTD.), Nutan™-K (TAKARA SHUZO CO. LTD.) and the like.

The cloned DNA can be used as is, or after digestion with a restriction enzyme or addition of a linker as desired, depending on the purpose of its use. The DNA may have the translation initiation codon ATG at the 5' end thereof, and the translation stop codon TAA, TGA or TAG at the 3' end thereof where necessary. These translation initiation codons and translation stop codons can be added by using a suitable synthetic DNA adaptor.

An expression vector containing a DNA encoding HGF can be produced, for example, by cleaving out an object DNA fragment from the DNA encoding HGF and connecting the DNA fragment with the downstream of a promoter in a suitable expression vector.

As expression vectors, plasmids derived from *Escherichia coli* (e.g., pBR322, pBR325, pUC12, pUC13); plasmids derived from *Bacillus subtilis* (e.g., pUB110, pTP5, pC194); plasmids derived from yeast (e.g., pSH19, pSH15); insect cell expression plasmids (e.g., pFast-Bac); animal cell expression plasmids (e.g., pA1-11, pXT1, pRc/CMV, pRc/RSV, pcDNAI/Neo); bacteriophages such as λ phage; insect virus vectors such as baculovirus (e.g., BmNPV, AcNPV); animal virus vectors such as retrovirus, vaccinia virus, adenovirus and adeno-associated virus, and the like are used.

The promoter may be any promoter appropriate for the host used to express the gene.

For example, when the host is an animal cell, cytomegalovirus (CMV) derived promoter (e.g., CMV immediate early promoter), human immunodeficiency virus (HIV) derived promoter (e.g., HIV LTR), Rous sarcoma virus (RSV) derived promoter (e.g., RSV LTR), mouse mammary tumor virus (MMTV) derived promoter (e.g., MMTV LTR), moloney murine leukemia virus (MoMLV) derived promoter (e.g., MoMLV LTR), herpes simplex virus (HSV) derived promoter (e.g., HSV thymidine kinase (TK) promoter), SV40 derived promoter (e.g., SV40 early promoter), Epstein-Barr virus (EBV) derived promoter, adeno-associated virus (AAV) derived promoter (e.g., AAV p5 promoter), adenovirus (AdV) derived promoter (Ad2 or Ad5 major late promoter) and the like are used.

When the host is an insect cell, polyhedrin promoter, P10 promoter and the like are preferable.

When the host is a bacterium of the genus *Escherichia*, the trp promoter, the lac promoter, the recA promoter, the λP$_L$ promoter, the 1 pp promoter, the T7 promoter and the like are preferred.

When the host is a bacterium of the genus *Bacillus*, the SPO1 promoter, the SPO2 promoter, the penP promoter and the like are preferred.

When the host is yeast, the PHO5 promoter, the PGK promoter, the GAP promoter, the ADH promoter and the like are preferred.

Useful expression vectors include, in addition to the above, expression vectors that optionally comprise an enhancer, a splicing signal, a polyA addition signal, a selection marker, an SV40 replication origin, and the like. As examples of the selection markers, the dihydrofolate reductase (dhfr) gene [methotrexate (MTX) resistance], the ampicillin resistance (Amp$^r$) gene, the neomycin resistance (Neo$^r$) gene (G418 resistance), and the like can be mentioned. In particular, when a dhfr gene deficient Chinese hamster (CHO-dhfr$^-$) cell is used and the dhfr gene is used as the selection marker, a target gene can also be selected using a thymidine-free medium.

In addition, where necessary, a base sequence (single codon) encoding a signal sequence suitable for the host may be added to the 5' end side of DNA encoding HGF. When the host is an animal cell, insulin signal sequence, α-interferon signal sequence, antibody molecule signal sequence and the like are used; when the host is the genus *Escherichia*, PhoA signal sequence, OmpA signal sequence and the like are used; when the host is the genus *Bacillus*, α-amylase signal sequence, subtilisin signal sequence and the like are used; and when the host is yeast, MFα signal sequence, SUC2 signal sequence and the like are used.

As the host, animal cell, insect cell, insect, genus *Escherichia*, genus *Bacillus*, yeast and the like are used.

As the animal cell, monkey derived cell (e.g., COS-1, COS-7, CV-1, Vero), hamster derived cell (e.g., BHK, CHO, CHO-K1, CHO-dhfr⁻), mouse derived cell (e.g., NIH3T3, L, L929, CTLL-2, AtT-20), rat derived cell (e.g., H4IIE, PC-12, 3Y1, NBT-II), human derived cell (e.g., HEK293, A549, HeLa, HepG2, HL-60, Jurkat, U937) and the like are used.

As the insect cell, established cell line derived from cabbage armyworm (*Spodoptera frugiperda* cell; Sf cell), MG1 cell derived from the mid-intestine of *Trichoplusia ni*, High Five™ cell derived from an egg of *Trichoplusia ni*, cell derived from *Mamestra brassicae*, cell derived from Estigmena acrea, and the like are used when the virus is AcNPV. When the virus is BmNPV, established cell line derived from *Bombyx mori* (*Bombyx mori* N cell; BmN cell) and the like are used. As the Sf cell, Sf9 cell (ATCC CRL1711), Sf21 cell (all above, Vaughn, J. L. et al., In Vivo, 13: 213-217 (1977)), and the like are used.

As the insect, a larva of *Bombyx mori* and the like are to used.

As the genus *Escherichia, Escherichia coli* K12, DH1, JM103, JA221, HB101, C600 and the like are used.

As the genus *Bacillus, Bacillus subtilis* MI114, 207-21 and the like are used.

As the yeast, *Saccharomyces cerevisiae* AH22, AH22R⁻, NA87-11A, DKD-5D, 20B-12, *Schizosaccharomyces pombe* NCYC1913, NCYC2036, *Pichia pastoris* KM71 and the like are used.

Transformation can be performed according to the choice of host by a commonly known method.

Animal cells can be transformed according to the method described in, for example, Cell Engineering additional volume 8, New Cell Engineering Experiment Protocol, 263-267 (1995) (published by Shujunsha), Virology, 52: 456 (1973).

An insect cell or insect can be transformed, for example, according to a method described in Bio/Technology, 6, 47-55 (1988) and the like.

Recombinant HGF can be separated and purified by a method known per se from a culture obtained by culturing the aforementioned transformant. For example, when HGF is extracellularly (outside fungus) secreted, a method including separating the culture supernatant from the culture by centrifugation or filtration etc., and the like is used. HGF contained in the obtained culture supernatant can be isolated and purified by a method known per. Useful methods include methods based on solubility, such as salting-out and solvent precipitation; methods based mainly on differences in molecular weight, such as dialysis, ultrafiltration, gel filtration, and SDS-polyacrylamide gel electrophoresis; methods based on differences in electric charge, such as ion exchange chromatography; methods based on specific affinity, such as affinity chromatography; methods based on differences in hydrophobicity, such as reverse phase high performance liquid chromatography; methods based on differences in isoelectric point, such as isoelectric focusing; and the like. These methods can be combined as appropriate.

When the thus-obtained HGF is a free form, the free form can be converted to a salt by a method known per se or a method based thereon; when the protein is obtained as a salt, the salt can be converted to a free form or another salt by a method known per se or a method based thereon.

HGF may be directly used as a drug substance, or can also be used after processing into a pharmaceutical composition by mixing with a pharmacologically acceptable carrier as necessary.

Here, as the pharmacologically acceptable carrier, various organic or inorganic carrier substances conventionally used as preparation materials are used, which are added as solvents, solubilizing agents, suspending agents, isotonic agents, buffering agents, soothing agents and the like for liquid preparations. Where necessary, preparation additives such as preservative, antioxidant, colorant and the like can also be used.

As examples of preferable solvents, water for injection, physiological saline, Ringer's solution, alcohols, propylene glycol, polyethylene glycol, sesame oil, corn oil, olive oil, cottonseed oil and the like can be mentioned.

As examples of preferable solubilizers, polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like can be mentioned.

As examples of preferable suspending agents, detergents such as stearyltriethanolamine, sodium lauryl sulfate, laurylaminopropionic acid, lecithin, benzalkonium chloride, benzethonium chloride, and glyceryl monostearate; hydrophilic polymers, for example, polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, polyoxyethylene hydrogenated castor oil and the like can be mentioned.

As examples of preferable isotonizing agents, sodium chloride, glycerin, D-mannitol, D-sorbitol, glucose and the like can be mentioned.

As examples of preferable buffers, buffer solutions such as of phosphates, acetates, carbonates and citrates, and the like can be mentioned.

As examples of preferable soothing agents, benzyl alcohol and the like can be mentioned.

As examples of preferable preservative, para-oxybenzoic acid esters, chlorobutanol, benzyl alcohol, phenethyl alcohol, dehydroacetic acid, sorbic acid and the like can be mentioned.

As examples of preferable antioxidant, sulfite, ascorbate and the like can be mentioned.

As examples of preferable colorant, water-soluble edible tar dyes (e.g., edible dyes such as edible red No. 2 and No. 3, edible yellow No. 4 and No. 5, and edible blue No. 1 and No. 2), water-insoluble lake dyes (e.g., aluminum salts of the aforementioned water-soluble edible tar dyes), natural dyes (e.g., β-carotene, chlorophyll, bengala and the like) and the like can be mentioned.

As examples of dosage forms for the above-described pharmaceutical composition, parenteral agent such as injection formulations (e.g., subcutaneous injections, intravenous injections, intramuscular injections, intraperitoneal injections and the like) and drip infusions can be mentioned.

A pharmaceutical composition can be produced by a method in common use in the field of formulated, for example, a method described in the Japanese Pharmacopoeia and the like. The content of the active ingredient in the pharmaceutical composition varies depending on dosage form, dose of the active ingredient and the like, and is, for example, about 0.1 to 100% by weight.

Preferable preparation for parenteral administration (e.g., intravenous injection, subcutaneous injection, muscle injection, topical injection, intraperitoneal administration and the like) includes aqueous and non-aqueous isotonic sterile injection solutions, which may contain antioxidant, buffer, bacteriostatic agent, isotonic agent and the like. In addition, aqueous and non-aqueous sterile suspensions can be mentioned, which may contain suspending agent, solubilizer, thickener, stabilizer, preservative and the like. The protein preparation can be sealed in a container by a unit dose such as ampoule and vial or plural doses. It is also possible to freeze-dry HGF and a pharmacologically acceptable carrier and preserve same in a state requiring dissolution or suspending in a suitable aseptic vehicle immediately before use.

Specific formulation methods of HGF are described in, for example, WO00/72873, WO90/10651, WO96/32960, WO99/27951, WO00/07615, JP-A-H6-247872, JP-A-H6-40938, JP-A-H9-25241, JP-A-H10-158190 and the like. The recombinant human HGF (rh-HGF) preparation used in the below-mentioned Examples was produced at a grade meeting the Good Manufacturing Practice (GMP), and is an aqueous injection containing 10 mg of rh-HGF in one vial (2 ml), which is diluted when in use with a diluting fluid containing 5 mg/ml arginine as a stabilizer and 0.01% polysorbate 80 as an anti-adsorption agent to give a final preparation.

Since an antibody to a hepatocyte surface molecule can specifically deliver a medicament to hepatocytes, in one embodiment of the present invention, HGF is crosslinked with the antibody to give an immunoconjugate which can improve the stability of HGF in blood and the efficiency of delivery to the hepatocyte surface. Examples of the hepatocyte surface molecule include, but are not limited to, EGFR (HER1), HER2, HER3, HER4 and the like. When an anti-EGFR antibody is used, a non-neutralizing antibody is desirably used as a targeting antibody, so that the signal transduction from EGFR will not be inhibited. The antibody to hepatocyte surface molecule may be any of polyclonal antibody and monoclonal antibody, and preferably monoclonal antibody. The antibody can be produced by a well-known immunological technique. The antibody may be a complete antibody molecule or a fragment. The fragment may be any as long as it has an antigen binding site (CDR) to a hepatocyte surface molecule and, for example, Fab, F(ab')$_2$, ScFv, minibody and the like can be mentioned.

An HGF preparation finally prepared as a liquid preparation as mentioned above can be administered to patients intravenously, intraarterially, subcutaneously, intramuscularly, intraperitoneally and the like by injection or drip infusion. While the dose is appropriately adjusted according to the symptom, age, body weight and the like of the patients, it is, for example, without limitation, an amount between 0.6 mg/m$^2$/day obtained by conversion, to human, of 0.1 mg/kg/day with confirmed effectiveness in rats as a result of non-clinical safety tests, and 24 mg/m$^2$/day obtained by conversion, to human, of 4.0 mg/kg/day with confirmed safety (reversibility of side effects) in rats as a result of non-clinical safety tests, which can be administered in one to several portions. For continuous stability of HGF in blood and reduction of the risk of expressing side effects, one administration is desirably given by drip infusion for a long time. For example, when the daily dose is administered in one portion, it is administered over 1-12 hr, preferably 2-6 hr. Particularly, to avoid a rapid decrease in the blood pressures due to HGF administration, it is desirable to administer systemically while increasing the administration rate stepwisely or continuously in one administration. Examples of a specific administration protocol include, but are not limited to, a method of intravenously administering about 10% of one dose in the first ⅓ of the single administration time, about 30% of one dose in the next ⅓ of the single administration time, and about 60% of one dose in the final ⅓ of the single administration time. Furthermore, as a means for avoiding the risk of a decrease in the blood pressure, a method including infusion of saline prior to HGF administration can be mentioned.

The administration period of HGF preparation is not particularly limited, and can be appropriately adjusted according to the symptoms and the like of the patients as long as sufficient efficacy can be obtained and severe side effects do not occur. It is, for example, 1-4 weeks, preferably about 10-20 days.

The dose and/or administration period of the HGF preparation can be appropriately increased or reduced based on the results of efficacy evaluation of HGF to be mentioned below.

The treatment target of the HGF preparation of the present invention is a patient with acute liver failure. The acute liver failure is defined as, of acute liver injury with various causes, a case showing prothrombin time (PT) of not more than 50% or Prothrombin Inhibition-International unit (PI-INR) of not less than 1.5. When hepatic encephalopathy with liver injury is of grade I coma or below, it is diagnosed as acute liver failure without hepatic coma. In about 30% of such cases, irreversible hepatocyte death progresses despite the treatment, and advances to fulminant hepatitis or late onset hepatic failure with encephalopathy with coma grade II or above. Fulminant hepatitis is identified as hepatitis showing PT of less than 40% of the standardized value, which develops hepatic encephalopathy within 8 weeks from the manifestation of the symptoms. Fulminant hepatitis is further classified into two subtypes: acute (FHA) and subacute (FHSA) (encephalopathy occurs within 10 days and later than 11 days, respectively). On the other hand, patients showing PT of less than 40%, who develop encephalopathy in 8-24 weeks from the manifestation of the symptoms, are diagnosed with late onset hepatic failure.

As shown in the below-mentioned Examples, the lifesaving rate based on a nationwide survey of the patients with fulminant hepatitis and late onset hepatic failure in our country was about 18%. However, two out of four patients could be saved by the treatment with the HGF preparation of the present invention, and one of the death cases showed a long-term survival of 68 days from the onset of hepatic encephalopathy. Therefore, the preparation was strongly suggested to show a treatment effect even for fulminant hepatitis and/or late onset hepatic failure showing extremely poor prognosis, for which a conventional effective treatment method was solely liver transplantation. The administration protocol of the HGF preparation used in the Examples includes a dose confirmed to have a liver regenerative action in experiments using normal rats and animals free of severe liver injury such as partially hepatectomized rats and the like, and a administration period predicted to be necessary and sufficient from the treatment results of fulminant hepatitis and late onset hepatic failure. Since the results of non-clinical safety tests predict that the dose can be increased to at least 4-fold at minimum without causing irreversible side effects, it is considered the lifesaving rate of patients with fulminant hepatitis and/or late onset hepatic failure can be further improved by optimizing the dose and the administration period. Furthermore, the treatment of patients with acute liver failure without hepatic coma, who are before progression to fulminant hepatitis or late onset hepatic failure, using the HGF preparation of the present invention can prevent progression (becoming fulminant) to fulminant hepatitis and/or late onset hepatic failure, and consequently, the progression suppressive effect can markedly reduce the mortality rate of acute liver failure patients.

The HGF preparation of the present invention can be used in combination with other treatment means for acute liver failure as necessary. As other treatment means that can be combined with HGF, for example, corticosteroid treatment [Tygstrup, N. & Juhl, E., Gut, 1979; 20:620-623], lamivudine administration for acute hepatitis B [Kumar, M. et al., Hepatology, 2007; 45:97-101], and a plasma exchange therapy [Clemmesen, J. O. et al., Am. J. Gastroenterol., 2001; 96:1217-1223] can be mentioned.

The present invention also provides a method for evaluating the efficacy of HGF, comprising measuring the amount of α-fetoprotein and/or soluble Fas in a sample collected from a liver injury patient administered with HGF.

Increase in the serum AFP value in acute liver failure was considered to be due to liver regeneration induced following liver injury (Taketa, K., Hepatology, 12: 1420-1432 (1990)). On the other hand, serum HGF value is important for predicting whether acute hepatitis becomes fluminant and prognosis prediction of fulminant hepatitis. In fulminant hepatitis, the serum HGF value increases to not less than 1.0 ng/ml (standard value not more than 0.40 ng/ml), whereas in 439 cases in the nationwide survey data (1998-2009) of fulminant hepatitis and late onset hepatic failure, no correlation was found between blood HGF value and serum AFP value. That is, in fulminant hepatitis and late onset hepatic failure patients, serum AFP value does not increase due to an increase in the blood HGF concentration by endogenous HGF induced in liver injury, and therefore, even when blood HGF concentration is increased by an exogenous administration of HGF (rh-HGF), an increase in the serum AFP level cannot be predicted. Under such situation, the present inventors repeatedly administered HGF to fulminant hepatitis and late onset hepatic failure patients and found that the serum AFP value unexpectedly increased during the administration period and gradually decreased after the completion of the administration, and clarified that AFP becomes an index (biomarker) of a liver regeneration promoting effect when patients with acute liver failure such as fulminant hepatitis, severe acute hepatitis, chronic hepatic failure such as decompensated cirrhosis and the like are treated with HGF. The liver weight (liver volume) and serum albumin value did not change much during the administration period, and it was shown that AFP reflects a real-time liver regenerative effect more sharply than conventionally-known liver regeneration promoting markers.

On the other hand, an index for monitoring the anti-apoptotic action of HGF in the human body has not been found heretofore. The present inventors have compared soluble Fas values in blood before and after repeated administration of HGF, and found that the serum soluble Fas value increases by HGF administration. Soluble Fas is a Fas present on a cell surface, which is cleaved and released into the blood, and binds to Fas ligand to antagonize the binding of Fas and Fas ligand on the cell surface, thus suppressing apoptosis. Therefore, it was shown that soluble Fas becomes an index (biomarker) of an apoptosis suppressive effect when patients with acute liver failure such as fulminant hepatitis, severe acute hepatitis, chronic hepatic failure such as decompensated cirrhosis and the like are treated with HGF.

The patient to be the evaluation target of the efficacy evaluation method of the present invention is not particularly limited as long as he/she has liver injury, and administered with HGF as a treatment thereof, and patients with various diseases associated with liver injury, hepatocyte death, such as acute liver failure (including fulminant hepatitis, late onset hepatic failure, acute liver failure without hepatic coma), acute hepatitis, chronic hepatitis, autoimmune liver diseases (autoimmune hepatitis, primary biliary cirrhosis), virus hepatitis (type A-E), hepatic fibrosis, cirrhosis, liver cancer, alcoholic liver injury, drug-induced liver injury (drug toxicity-induced liver injury, drug allergy-induced liver injury), liver abscess, parasitic liver disease (schistosomiasis japonica, clonorchiasis), hepatic amyloidosis, lupoid hepatitis) and the like can be mentioned, with preference given to acute liver failure patients.

While a sample derived from a patient to be a test sample in the efficacy evaluation method of the present invention is not particularly limited as long as it can detect an increase in AFP associated with the liver regenerative effect and/or an increase in soluble Fas associated with the hepatocyte anti-apoptotic effect, it is preferably less invasive to the patients. Examples thereof include samples easily collected from the body such as blood, plasma, serum, saliva, urine, lacrimal fluid and the like, and those collected comparatively easily such as cerebrospinal fluid, bone marrow fluid, pleural effusion, ascites fluid, synovial fluid, aqueous humor, vitreous humor and the like. More preferred are serum and plasma.

When serum and plasma are used, they can be prepared by collecting blood samples from patients by a conventional method and separating the liquid component.

AFP and/or soluble Fas in a test sample can be detected by, for example, subjecting the sample to a method combining various molecular weight determination methods such as gel electrophoresis, various separation and purification methods (e.g., ion exchange chromatography, hydrophobic chromatography, affinity chromatography, reversed-phase chromatography and the like), ionization methods (e.g., electron impact ionization method, field desorption method, secondary ionization method, fast atom bombardment method, matrix-assisted laser desorption ionization (MALDI) method, electrospray method and the like), is mass spectrometers (e.g., double-focusing mass spectrometer, quadrupol mass spectrometer, time-of-flight mass spectrometer, Fourier-transform mass spectrometer, ion cyclotron mass spectrometer and the like) and the like and detecting a band or spot, or a peak that matches with the molecular weight of the marker protein, though the method is not limited to these methods. Since the amino acid sequences of AFP and soluble Fas are known, a method including preparing an antibody that recognizes the amino acid sequence, and detecting the protein by Western blotting, various immunoassays (e.g., ELISA) is more preferably used. Furthermore, the hybrid-type detection method mentioned above is also effective.

The measurement of AFP and soluble Fas is particularly useful since the protein can be detected highly sensitively and highly accurately without using a special apparatus such as mass spectrometer, by using a kit formed to contain antibodies thereto and a constructed optimized immunoassay system.

An antibody to AFP or soluble Fas can be prepared by, for example, isolating and purifying the protein from a human sample expressing same, and immunizing an animal with the marker protein or a partial peptide thereof as an antigen.

An antibody to AFP or soluble Fas may be any of polyclonal antibody and monoclonal antibody, and can be produced by a well-known immunological method. The antibody includes not only a complete antibody molecule but a fragment thereof and, for example, Fab, F(ab')$_2$, ScFv, minibody and the like can be mentioned.

For example, a polyclonal antibody can be obtained by subcutaneously or intraperitoneally administering AFP or soluble Fas or a partial peptide thereof (where necessary, a complex crosslinked with a carrier protein such as bovine serum albumin, KLH (Keyhole Limpet Hemocyanin) and the like can also be formed) as an antigen together with a commercially available adjuvant to an animal about 2 to 4 times at 2-3 weeks' intervals (antibody titer of partially collected serum is measured by a known antigen-antibody reaction, and an increase therein is confirmed), collecting the whole blood about 3-about 10 days from the final immunization, and purifying the antiserum. As an animal to be administered with an antigen, mammals such as rat, mouse, rabbit, goat, guinea pig, hamster and the like can be mentioned.

A monoclonal antibody can also be prepared by a cell fusion method (e.g., Takeshi Watanabe, saibouyugouhou no genri to monokuronaru kotai no sakusei, Akira Taniuchi and Toshitada Takahashi, eds., "monokuronaru kotai to gan-kiso to rinsho-", pp. 2-14, Science Forum Publishing, 1985). For example, AFP or soluble Fas or a partial peptide thereof is subcutaneously or intraperitoneally administered together with a commercially available adjuvant to a mouse 2-4 times, the spleen or lymph node is collected about 3 days from the final administration, and lymphocytes are recovered. The lymphocytes and myeloma cells (e.g., NS-1, P3X63Ag8 and the like) are subjected to cell fusion to give a hybridoma that produces a monoclonal antibody to AFP or soluble Fas. The cell fusion may be performed by a PEG method [J. Immunol. Methods, 81(2): 223-228 (1985)] or a voltage pulsation method [Hybridoma, 7(6): 627-633 (1988)]. A hybridoma that produces the desired monoclonal antibody can be selected by detecting in the culture supernatant an antibody that specifically binds to an antigen using well-known EIA, RIA, or the like. Cultivation of a hybridoma that produces a monoclonal antibody can be conducted in vitro, or in vivo in mice or rats, preferably in mouse ascites fluid and the like, and the antibody can be obtained from a hybridoma culture supernatant or animal ascites fluid, respectively.

The efficacy evaluation method of the present invention using an anti-AFP or anti-soluble Fas antibody is not subject to limitation, and any method of measurement can be used as long as it is a measurement method wherein the amount of antibody, antigen or antibody-antigen complex corresponding to the amount of antigen in the test sample is detected by a chemical or physical means and is calculated from a standard curve generated using standard solutions containing known amounts of antigen. For example, nephelometry, the competitive method, the immunometric method, the sandwich method and the like are preferably used.

As examples of the labeling agent used for the assay using a labeling substance, a radioisotope, an enzyme, a fluorescent substance, a luminescent substance and the like can be used. As examples of the radioisotope, [$^{125}$I], [$^{131}$I], [$^{3}$H], [$^{14}$C] and the like can be used. As the above-described enzyme, those that are stable and high in specific activity are preferred; for example, β-galactosidase, β-glucosidase, alkaline phosphatase, peroxidase, malate dehydrogenase and the like can be used. As examples of the fluorescent substance, fluorescamine, fluorescein isothiocyanate and the like can be used. As examples of the luminescent substance, luminol, luminol derivative, luciferin, lucigenin and the like can be used. Furthermore, a biotin-avidin system can also be used for binding of an antibody or an antigen and a labeling agent.

In insolubilizing the antigen or antibody, physical adsorption may be used, and a chemical bond in common use to insolubilize or immobilize a protein or an enzyme or the like, may also be used. As the carrier, insoluble polysaccharides such as agarose, dextran and cellulose, synthetic resins such as polystyrene, polyacrylamide and silicone, glass and the like can be mentioned.

In the sandwich method, the amount of AFP or soluble Fas in a test sample can be quantified by reacting the test sample with an anti-AFP or anti-soluble Fas antibody insolubilized (primary reaction) and further reacting with another anti-AFP or anti-soluble Fas antibody labeled (secondary reaction), and thereafter measuring the amount (activity) of the labeling agent on the insolubilizing carrier. The primary reaction and the secondary reaction may be conducted in the reverse order, and may be conducted simultaneously or after a time lag.

A monoclonal antibody to AFP or soluble Fas can be used for a measurement system other than the sandwich method, for example, the competitive method, the immunometric method or nephelometry and the like.

In the competitive method, antigen in a test sample and labeled antigen are competitively reacted with an antibody, a non-reacted labeled antigen (F) and a labeled antigen (B) bonded to the antibody are separated (B/F separation), the amount of label of B or F is measured to quantify the amount of the antigen in the test sample. For this reaction method, a liquid phase method wherein a soluble antibody is used as the antibody, and polyethylene glycol and a secondary antibody against the aforementioned antibody and the like are used for B/F separation, and a solid-phase method wherein a solid-phase antibody is used as a primary antibody, or a soluble primary antibody is used and a solid-phase antibody is used as a secondary antibody are employed.

In the immunometric method, antigen in a test sample and solid-phase antigen are competitively reacted with a given amount of a labeled antibody, and the solid phase and the liquid phase are separated, or antigen in a test sample and an excess amount of a labeled antibody are reacted, solid-phase antigen is added to bond a non-reacted labeled antibody to the solid phase, and the solid phase is separated from the liquid phase. Then, the amount of the label of either phase is measured and the amount of antigen in the test sample is quantified.

Also, in nephelometry, the amount of insoluble precipitate resulting from an antigen-antibody reaction in the gel or in the solution is measured. Even when the amount of antigen in the test sample is small and only a small amount of precipitate is obtained, laser nephelometry, which utilizes laser scattering, and the like are preferably used.

In applying these individual immunological measurement methods to the quantification method of the present invention, it is unnecessary to set special conditions, procedures and the like. Making ordinary technical considerations for those skilled in the art to the ordinary conditions and procedures in each method, a measurement system for AFP or soluble Fas can be constructed. For details of these general technical means, compendia, books and the like can be referred to.

For example, edited by Hiroshi Irie, "Rajioimunoassei" (Kodansha, published in 1974), edited by Hiroshi Irie, "Zoku Rajioimunoassei" (Kodansha, published in 1979), edited by Eiji Ishikawa et al., "Kouso Meneki Sokuteihou" (Igaku-Shoin, published in 1978), edited by Eiji Ishikawa et al., "Kouso Meneki Sokuteihou" (2nd edition) (Igaku-Shoin, published in 1982), edited by Eiji Ishikawa, "Kouso Meneki Sokuteihou" (3rd edition) (Igaku-Shoin, published in 1987), "Methods in ENZYMOLOGY", Vol. 70 (Immunochemical Techniques (Part A)), ibidem, Vol. 73 (Immunochemical Techniques (Part B)), ibidem, Vol. 74 (Immunochemical Techniques (Part C)), ibidem, Vol. 84 (Immunochemical Techniques (Part D: Selected Immunoassays)), ibidem, Vol. 92 (Immunochemical Techniques (Part E: Monoclonal Antibodies and General Immunoassay Methods)), ibidem, Vol. 121 (Immunochemical Techniques (Part I: Hybridoma Technology and Monoclonal Antibodies)) (all published by Academic Press) and the like can be referred to.

When the level of AFP in a sample derived from a patient administered with HGF, which is measured by any of the above-mentioned methods, significantly increases as compared to that in a sample obtained from the patient before administration of HGF, it is judged that liver regeneration is induced in the patient and the efficacy of HGF administration is found. On the other hand, when the level of AFP in a sample derived from a patient administered with HGF does not change significantly or decreases as compared to that in a sample obtained from the patient before administration of HGF, it is judged that liver regeneration is not induced in the patient and the liver regeneration promoting effect by HGF administration is not found. In the latter case, when the anti-apoptotic effect using soluble Fas as an index is sufficient, the scheduled administration protocol may be performed as it is. When such effect is not obtained sufficiently, an increase of the HGF dose and/or extension of the administration period may be considered.

When the level of soluble Fas in a sample derived from a patient administered with HGF, which is measured by any of the above-mentioned methods significantly increases as compared to that in a sample obtained from the patient before administration of HGF, it is judged that apoptosis of hepatocyte is suppressed in the patient and the efficacy of HGF administration is found. On the other hand, when the level of soluble Fas in a sample derived from a patient administered with HGF does not change significantly or decreases as compared to that in a sample obtained from the patient before administration of HGF, it is judged that apoptosis of hepatocyte is not suppressed in the patient and the anti-apoptotic effect of hepatocyte (hepatoprotective effect) by HGF administration is not found. In the latter case, when the liver regeneration promoting effect using AFP as an index is sufficient, the scheduled administration protocol may be performed as it is. When such effect is not obtained sufficiently, an increase of the HGF dose and/or extension of the administration period may be considered.

The efficacy evaluation method of the present invention is preferably performed by collecting samples from patients in time series, measuring the amount of AFP and/or soluble Fas in each sample, and examining the time-course changes thereof. While the sample collection intervals are not particularly limited, it is desirable to collect samples as frequently as possible as long as the QOL of patients is not impaired. For example, when plasma or serum is used as a sample, blood samples are preferably collected at intervals of, for example, 1-10 days, preferably 3-7 days. When the level of AFP increases over time, it is judged that liver regeneration is induced in the patient and the efficacy of HGF administration is found. On the other hand, when the level of AFP does not change significantly or decreases over time, it is judged that liver regeneration is not induced in the patient and the liver regeneration promoting effect by HGF administration is not found. In the latter case, when the anti-apoptotic effect using soluble Fas as an index is sufficient, the scheduled administration protocol may be performed as it is. When such effect is not obtained sufficiently, an increase of the HGF dose and/or extension of the administration period may be considered.

When the level of soluble Fas increases over time, it is judged that apoptosis of hepatocyte is suppressed in the patient and the efficacy of HGF administration is found. On the other hand, when the level of soluble Fas does not change significantly or decreases over time, it is judged that apoptosis of hepatocyte is not suppressed in the patient and the anti-apoptotic effect on hepatocytes (hepatoprotective effect) by HGF administration is not found. In the latter case, when the liver regeneration promoting effect using AFP as an index is sufficient, the scheduled administration protocol may be performed as it is. When such effect is not obtained sufficiently, an increase of the HGF dose and/or extension of the administration period may be considered.

When AFP is an index in the efficacy evaluation method of the present invention, the evaluation target patient is desirably free of administration of a steroid-based anti-inflammatory agent. Since AFP expression is known to be influenced by the glucocorticoid response element (GRE) present at the 5' flanking region of AFP gene [Ido, A. et al., Cancer Res., 1995; 55:3105-3109], the liver regenerative effect by HGF administration may not be accurately reflected. Therefore, for patients concurrently using a steroid-based anti-inflammatory agent, the efficacy of HGF can be evaluated by placing importance on the judgment of the anti-apoptotic effect on hepatocytes using soluble Fas as an index.

The present invention also provides an HGF efficacy evaluation kit containing an anti-AFP antibody and/or an anti-soluble Fas antibody. The kit may further contain other elements preferable for practicing the above-mentioned efficacy evaluation method of the present invention, such as reaction buffer, washing, insolubilizing carrier, label, AFP and/or soluble Fas standard products and the like.

As mentioned above, when the efficacy of HGF is not found or the level thereof is found to be insufficient in a patient by the efficacy evaluation method of the present invention, an increase of the HGF dose and/or extension of the administration period may be considered. Therefore, the HGF preparation of the present invention is preferably used in combination with the efficacy evaluation kit of the present invention.

The present invention is explained in more detail in the following by referring to Examples, which are not to be construed as limiting the scope of the present invention.

EXAMPLES (Method)
Animal Experiment to Ensure Safety of rh-HGF Administration Animal Crown miniature swine (female, 6-7 months of age) and Wistar rats (male, 7 weeks of age) were purchased from Japan Farm (Kagoshima, Japan) and Charles River Laboratories Japan Inc. (Yokohama, Japan), respectively. The animals were maintained under constant room temperature (25° C.), and given free access to water and the indicated diet throughout the study period. The protocol for animal studies was approved by the ethics committee of the Graduate School of Medicine, Kyoto University (Kyoto, Japan). All animal experiments were performed after one to three weeks acclimation on a standard diet.

General Pharmacological Test

Crown miniature swine (female) were anesthetized by inhalation of sevoflurane, nitric dioxide and oxygen, catheters were inserted into one internal jugular vein (for injection of rh-HGF) and to one common carotid artery (to measure BP). 1 mg/kg of rh-HGF was injected through the internal jugular vein over the course of 20 min. HR was recorded by electrocardiographic monitoring, and cardiac function was measured via echocardiography. To evaluate the effect of stepwise injection of rh-HGF on BP, 0.4 mg/kg of rh-HGF was injected over the course of three hours, with a stepwise increase in the administration rate (10% of the total dose for the first 60 min, 30% for the next 60 min, and 60% for the last 60 min) through the catheter inserted into an internal jugular vein.
Evaluation of Renal Toxicity of Repeated Administration of rh-HGF rh-HGF (0.4, 1.0 and 4.0 mg/kg) was administered to rats intravenously in a bolus for 14 days, followed by observation for 2 weeks. Urinary excretion of albumin and protein were measured with time during and after rh-HGF administration. Animals were sacrificed at the ends of rh-HGF administration (day 14) and the observation period (day 28) to evaluate renal involvement, including serum creatinine and histological findings.
A Phase I/II Clinical Trial for Patients with Acute Liver Failure
Overview This single-arm, open-labeled, and dose-escalation study was conducted at Kyoto University Hospital (Kyoto, Japan). Study protocols were reviewed and approved by the Institutional Review Board and Ethics Committee governing Kyoto University Hospital before the commencement of patient enrollment. Studies were performed in accordance with principles of GCP, and conformed to ethical guidelines of the Declaration of Helsinki. All participating patients, or (when participants were not able to subscribe because of hepatic encephalopathy) their legal representatives provided written informed consent before being enrolled into the study.
Selection of Patients Consenting patients were prospectively screened from September 2005 to June 2008. Patients with FHSA or LOHF, who were not able to receive liver transplantation but met at least one of the following four parameters, were eligible: (1) aged 45-year-old or above, (1) PT 10% or less of the standardized values, (3) total bilirubin (T-Bil) level of 18.0 mg/dL or more, or (4) direct/total bilirubin ratio less than 0.67. The following patients were not eligible: those under 16 years old; those treated with glucagon and insulin, or prostaglandin E1 48 hours before registration; those with presence or past-history of malignant tumors; those with heart failure; those with severe complication including pneumonia, sepsis, disseminated intravascular coagulation syndrome or gastrointestinal bleeding; and those with allergic reaction against rh-HGF. Pregnancy-aged women were also ineligible, because toxicity of rh-HGF to reproductive development in female has not been examined. Additionally, patients with renal involvement, including urinary excretion of mg/mL protein, deformed red blood cells or red blood cell casts (RBC casts) in sedimentary urine, a serum creatinine level of 2.0 mg/dL or more, or urine volume less than 400 mL/day were also excluded.
Protocol Therapy and Observation after rh-HGF Administration Period rh-HGF was prepared as a GMP-grade material. The initial dose of rh-HGF was fixed at 0.6 mg/m$^2$/day, which was determined as a dose that ensures safety and clinical efficacy by several preclinical animal studies. In dose escalation study, the dose of rh-HGF can be increased from the initial dose (0.6 mg/m$^2$) to 1.2, 1.8 or 2.4 mg/m$^2$. rh-HGF was administered intravenously with a stepwise increase during 3 hr for up to 14 days, after which the patients were observed for 14 days. All patients were followed in order to determine the outcomes after the study period (up to 28 days).
End Points The first endpoint was the safety of repeated intravenous administration of rh-HGF, and was evaluated on the basis of the occurrence, frequency, and severity of adverse events. All patients were treated in an intensive care unit. During the study period, the patients were monitored periodically for safety from the start of rh-HGF administration to after the completion of study drug administration. Safety assessments were performed by physical examination, clinical test and the observation of adverse events. Adverse events were monitored throughout the duration of the study, and graded according to the Common Toxicity Criteria grading system. Causal association of adverse events with rh-HGF was determined by clinician's best judgment. All adverse events were treated appropriately regardless of the cause; where necessary, patients were withdrawn from the study. The incidence of adverse events was calculated from the number of patients experiencing at least one adverse event from among those who received at least a single dose of rh-HGF.

The secondary endpoints were the pharmacokinetics of intravenously injected rh-HGF and clinical efficacy, including survival period and outcome. To examine pharmacokinetics of rh-HGF, blood samples were collected at multiple time points on days 1, 3, 5, 8, and 11. Serum concentrations of HGF were determined by enzyme-linked immunosorbent assay (ELISA) (Otsuka Co., Ltd., Tokushima, Japan) (Tsubouchi et al., Hepatology 1991, 13:1-5). Test data, including PT-international normalized ratio (PT-INR), T-Bil, serum albumin, alanine aminotransferase (ALT), and α-fetoprotein (AFP), were examined before plasma exchange or rh-HGF administration. As for serum soluble Fas value, blood samples were collected before rh-HGF administration and the next day of the completion of the administration and measured.

Reference Example 1

Establishment of rh-HGF Administration Method to Respond to a Decrease in Blood Pressure in Miniature Swine In general pharmacological tests, intravenous administration of rh-HGF (1.0 or 0.2 mg/kg) caused a rapid decrease in systolic blood pressure (systolic BP) in miniature swine, whereas respiratory status was not affected. Therefore, before starting the clinical test, we further investigated the effect of rh-HGF on circulatory status in miniature swine under general anesthesia. When a total dose of rh-HGF of 1.0 mg/kg was administered over the course of 20 min, a decrease in systolic BP occurred promptly, and continued throughout rh-HGF administration (FIG. 1A). Although heart rate (HR) gradually decreased, no electrocardiographic abnormalities, including arrhythmia and ischemic changes, were observed throughout the experimental period. Additionally, echocardiography showed a decrease in left ventricular end-diastolic volume (LVEDV) as well as ejection fraction (EF), in parallel with a decrease in blood pressure, but no abnormalities of left ventricular movement (FIG. 1A). These results indicate that intravenous injection of rh-HGF reduced blood pressure through dilatation of capacitance vessels.

Next, a method for rh-HGF administration that would avoid rapid blood pressure reduction was developed. Finally, a stepwise injection method for increasing rh-HGF stepwisely for 3 hr (10% of the total dose for the first 60 min, 30% for the next 60 min, and 60% for the last 60 min) was established (FIG. 1B). The present inventors found that appropriate injection effectively prevented the decrease in blood pressure caused by intravenous rh-HGF administration (FIG. 10). This preventive effect also supports that dilatation of capacitance vessels is a cause of HGF-induced blood pressure reduction.

Reference Example 2

Figure 2:
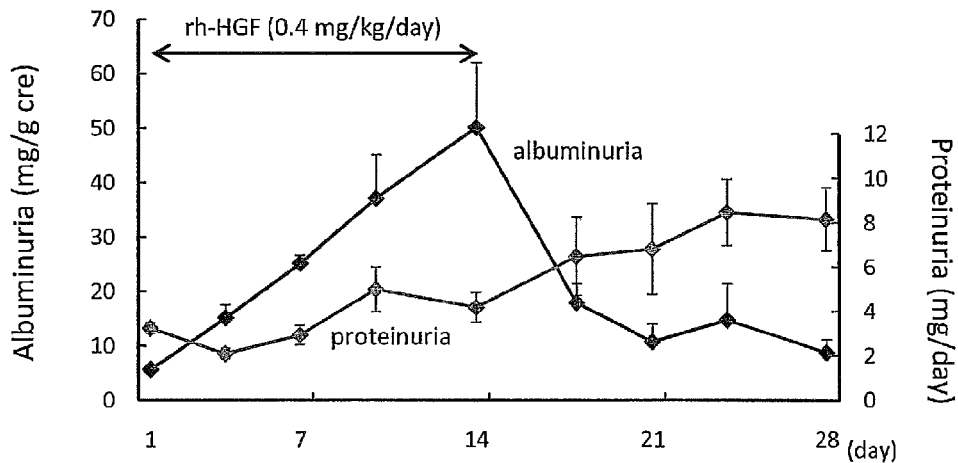
FIG. 2 shows that repeated administration of rh-HGF induces an increase in urinary excretion of albumin and protein in rats. Rats were administered rh-HGF, 0.4 (A), 1.0 (B), and 4.0 mg/kg/day (C) (n=4 for each), intravenously for 14 days, and urinary excretion of albumin and protein was measured before (day 1), during (days 7 and 14), and 7 and 14 days after HGF administration. Repeated administration of rh-HGF induced an increase in urinary albumin excretion in dose dependent manner. Urinary excretion of albumin was reversible even when administrating 4.0 mg/kg/day of rh-HGF (C). In addition, urinary excretion of albumin preceded an increase in proteinuria in rats treated with 0.4 and 1.0 mg/kg of rh-HGF (A and B, respectively).
Figure 2:
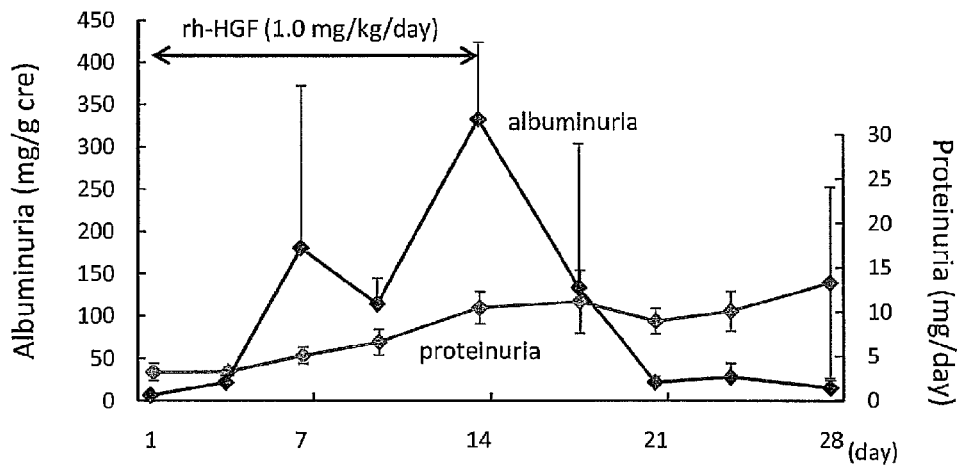
Figure 2:
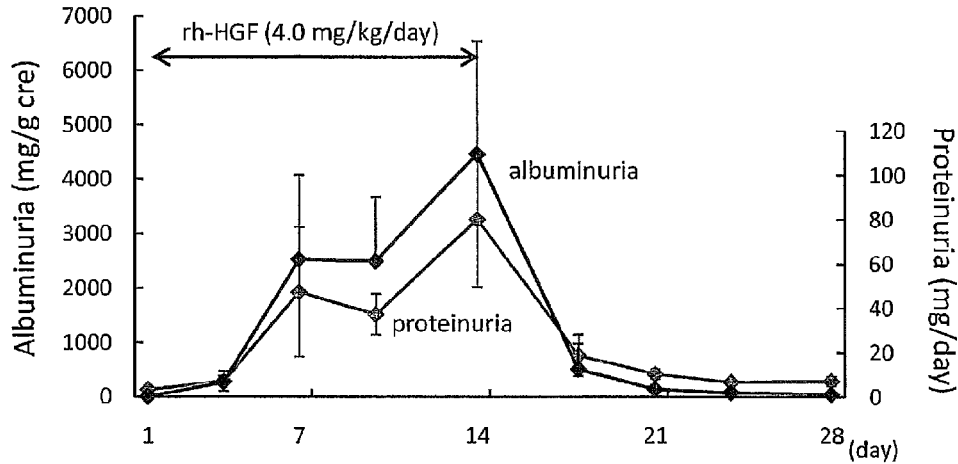

Evaluation of Renal Toxicity Induced by Repeated Administration of rh-HGF in Rats Repeated administration toxicity tests using rats or cynomolgus monkeys identified an increase in urinary excretion of albumin and protein as a potential adverse event in a clinical test. Therefore, we further examined whether renal toxicity induced by repeated rh-HGF administration for 14 days was reversible. 0.4, 1.0, and 4.0 mg/kg/day of rh-HGF were administered to rats for 14 days, after which the rats were observed for 14 days. Urinary excretion of albumin increased in rats treated with rh-HGF from day 4 in a dose dependent manner (FIG. 2). In rats treated with 0.4 or 1.0 mg/kg/day of rh-HGF, urinary excretion of albumin preceded an increase in proteinuria (FIGS. 2A and B). However, neither serum creatinine nor BUN were affected throughout the experimental period. In addition, urinary excretion of albumin gradually decreased after the completion of rh-HGF administration during the 14-day observation period. In histological analysis, mesangial proliferation, hyaline droplet deposition in glomeruli and tubules, and renal hypertrophy were observed after repeated administration of rh-HGF for 14 days. However, it was also confirmed that these histological findings were in the slight-to-mild range and reversible changes. Since rh-HGF dose of 0.1 mg/kg in rodents corresponds to 0.6 mg/m$^2$ in human, the daily dose in the clinical test was set to 0.6 mg/m$^2$.

Example rh-HGF Administration Phase I/II Trial in Subacute Fulminant Hepatitis (FHSA) and Late Onset Hepatic Failure (LOHF) Patients (1) Patient Characteristics Between September 2005 and June 2008, 20 patients with FHSA or LOHF were evaluated for participation in the clinical test of rh-HGF. As a result, 16 patients were excluded because they met one or more of the exclusion criteria, and only 4 patients were finally enrolled. Fulminant hepatitis is a relatively rare syndrome in Japan (698 patients between 1998 and 2003), and the patients with severe complications were excluded so as to more precisely evaluate the safety and efficacy of the therapy, which made the recruitment of trial subjects difficult. For this reason, the dose escalation study was not performed, and the same dose of 0.6 mg/m$^2$/day as the initial dose was administered to all patients throughout the administration period. The age of the participating subjects was 40-71 years old and two men and two women were involved (Table 1).

TABLE 1

| Patient characteristics | | | | |
|---|---|---|---|---|
| | Patient number | | | |
| | 1 | 2 | 3 | 4 |
| Age/Gender | 67/male | 71/female | 64/female | 40/male |
| Diagnosis results/ | FHSA/ | FHSA/ | LOHF/ | FHSA/ |
| Etiology | HEV | unknown | unknown | drug |
| Reason for not receiving LT | donor[1] | age[2] | donor[1] | donor[1] |
| Before rh-HGF administration | | | | |
| Grade of HE | II | II | V | 0 |
| Prothrombin time INR (%) | 2.07 (33) | 1.55 (49) | 1.78 (37) | 1.62 (43) |

TABLE 1-continued

| Patient characteristics | | | | |
|---|---|---|---|---|
| | Patient number | | | |
| | 1 | 2 | 3 | 4 |
| Albumin (g/dL) | 2.9 | 3.2 | 2.9 | 2.9 |
| T-Bil (mg/dL) | 11.2 | 6.9 | 11.7 | 27.6 |
| Direct/total bilirubin ratio | 0.58 | 0.41 | 0.44 | 0.71 |
| ALT (IU/L) | 32 | 131 | 260 | 253 |
| Serum HGF (ng/mL) | 0.77 | 1.94 | 1.07 | 1.88 |
| AFP (ng/dL) | 7 | 22.9 | 3.9 | 39.7 |
| Liver volume (mL) | 1055 | 595 | 640 | 1110 |
| Days between HE and rh-HGF administration (days) | 7 | 5 | 5 | 5 |
| rh-HGF administration period (days) | 13 | 14 | 12 | 14 |
| Outcome | | | | |
| during the study period | alive | alive | dead | alive |
| during the follow-up period | dead | alive | — | alive |

FHSA: subacute fulminant hepatitis;
LOHF: late onset hepatic failure;
HEV: hepatitis E virus infection
LT: liver transplantation;
HE: hepatic encephalopathy
[1]lack of an appropriate donor.
[2]70 years old or more.

Patients 1, 2 and 4 were diagnosed as FHSA, and patient 3 as LOHF. None of them could receive a liver transplantation since patients 1, 3, and 4 lacked appropriate donors, and patient 2 was over 70 years old. FHSA in patients 1 and 4 was caused by HEV and a supplement containing coenzyme Q-10, respectively, and the cause of hepatic failure in patients 2 and 3 was undetermined. Two patients with FHSA (patients 1 and 2) and one with LOHF (patient 3) exhibited hepatic encephalopathy at coma grade II and V, respectively, the consciousness level of patient 4 with FHSA was not impaired at the time of enrollment. In all patients, markedly prolonged prothrombin time (PT) and an increase in total bilirubin (T-Bil) and serum HGF were observed. Patient 2, with FHSA, and patient 3, with LOHF, showed reduced liver volume when determined by CT volumetry upon enrollment.

Figure 4:
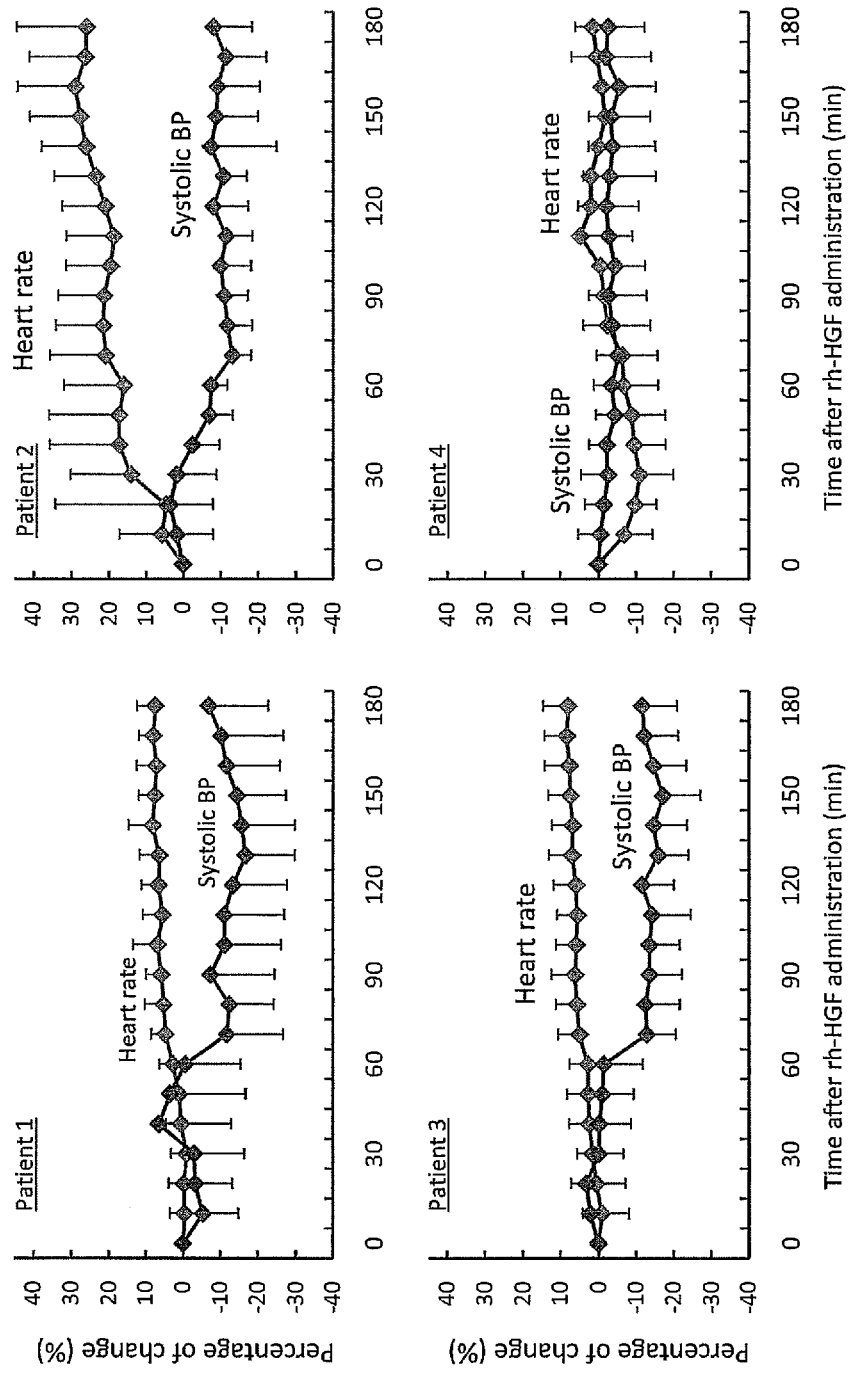
FIG. 4 shows that the blood pressure decreased during injection of rh-HGF in subacute fulminant hepatitis (patients 1, 2 and 4) and late onset hepatic failure (patient 3). Systolic blood pressure (systolic BP) and heart rate (HR) were monitored during rh-HGF injection for 3 hr. Intravenous injection of rh-HGF (0.6 mg/m$^2$) reduced the systolic blood pressure and increased the heart rate in patients 1, 2 and 3. Blood pressure reduction during rh-HGF injection did not affect the patients' general condition. Blood pressure immediately recovered following the completion of rh-HGF administration.
Figures 1, 7:
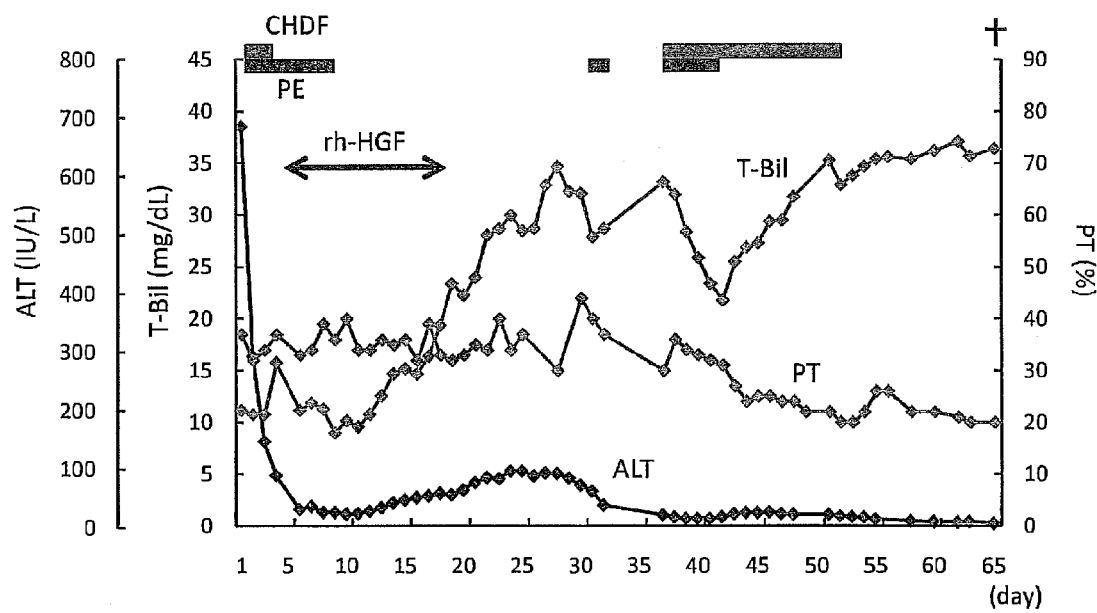
Figures 2, 7:
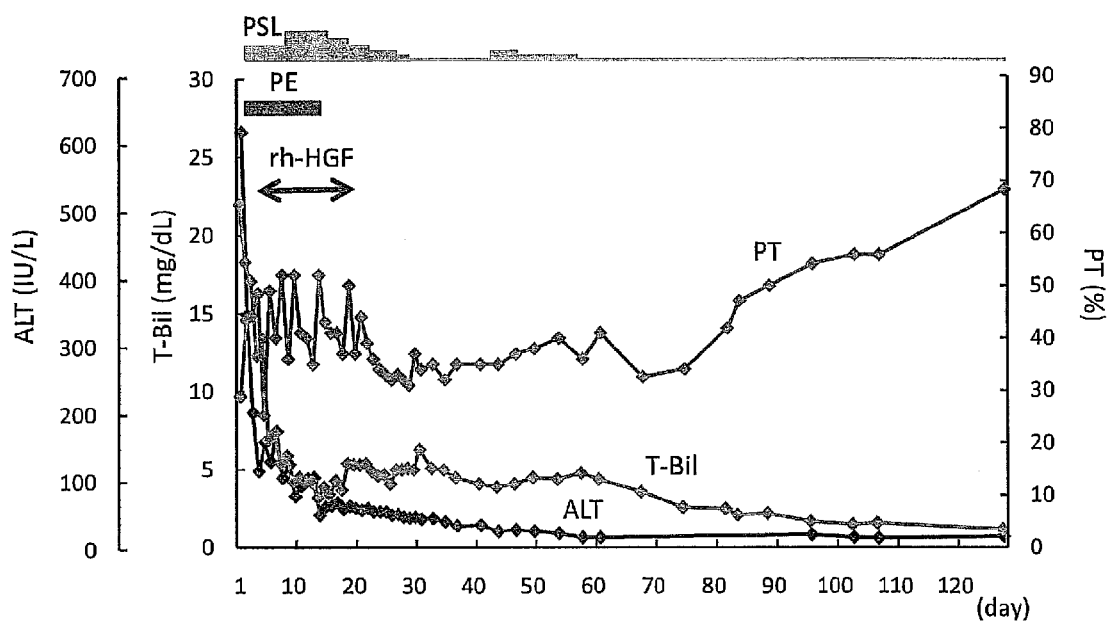
Figures 3, 7:
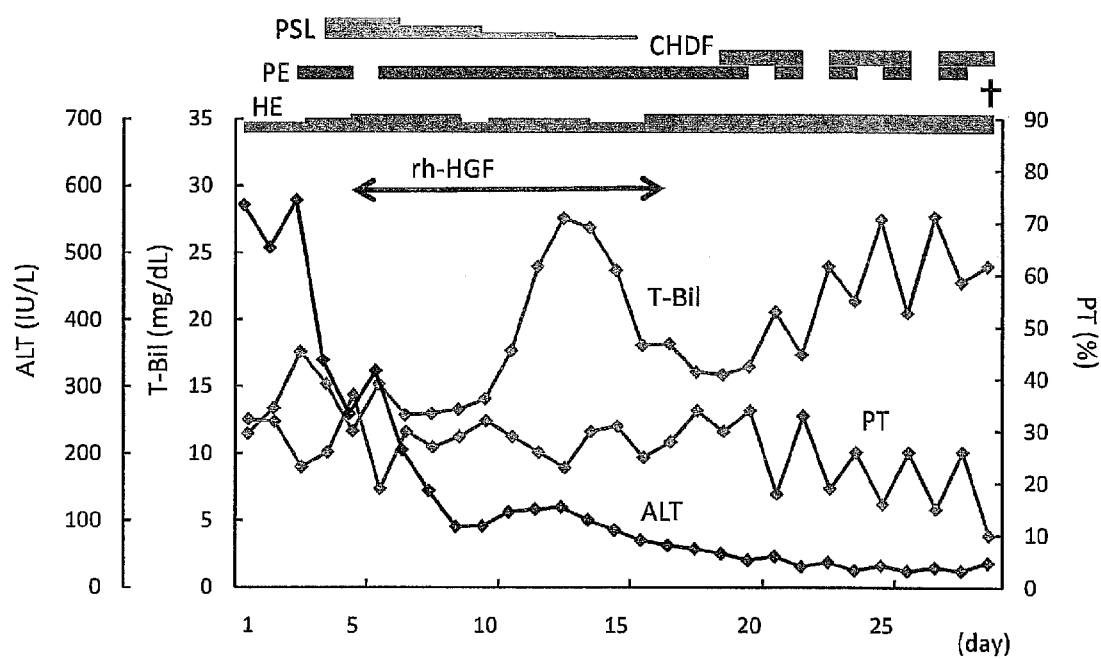
Figures 4, 7:
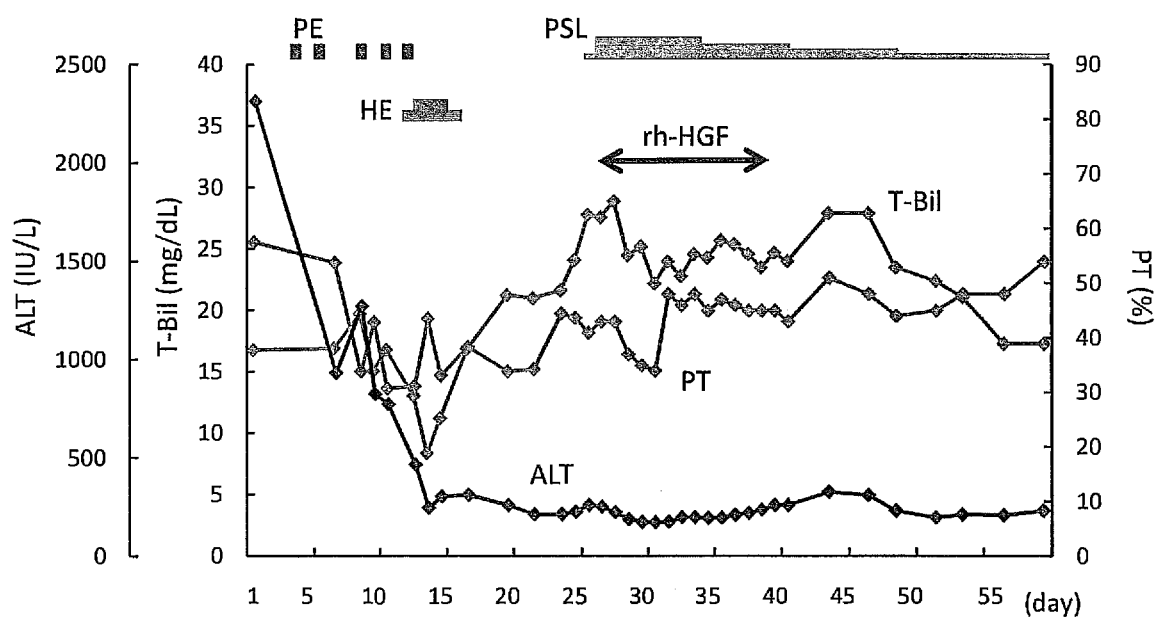

Treatment with rh-HGF was started between 5 and 7 days after development of hepatic encephalopathy. rh-HGF (0.6 mg/m$^2$/day) was intravenously administered for 14 days in patients 2 and 4. Patients 1 and 3 required cessation of rh-HGF administration on days 14 and 13, respectively, because of increased serum creatinine (2.1 mg/dL) and oliguria, respectively. All these symptoms were determined to accompany hepatic failure, not rh-HGF administration. Accordingly, the rh-HGF administration period was total 13 days and 12 days, respectively, in these patients. Plasma exchange was performed in all patients. Three patients, except for patient 1 with FHSA caused by HEV, were treated with corticosteroid (FIGS. 7-1-7-4). Finally, two of the patients with FHSA (patients 2 and 4) survived, but patient 1 with FHSA died after the completion of the study period, and patient 3 with LOHF died during the study period (Table 1 and FIGS. 7-1-7-4).

(2) Pharmacokinetic of Stepwise Gradual Injection of rh-HGF

Figure 3:
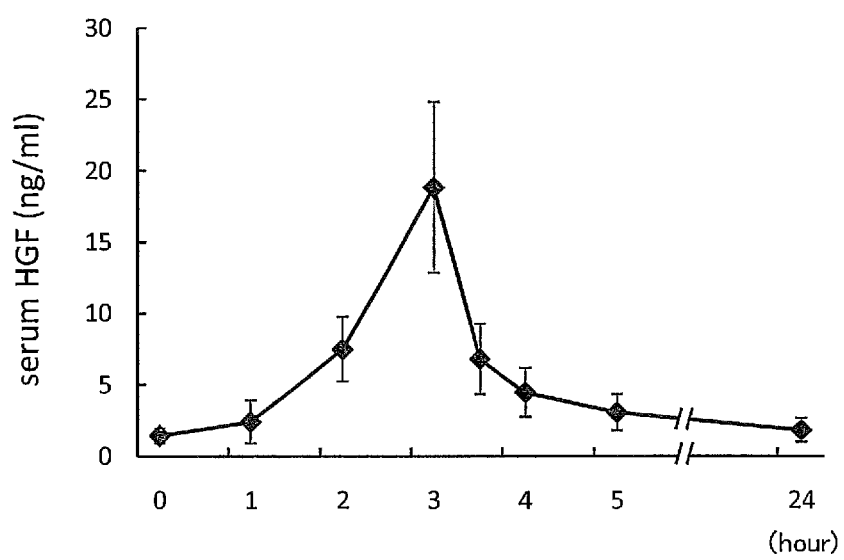
FIG. 3 shows a shift of serum HGF concentration during and after rh-HGF administration. rh-HGF ($0.6$ mg/m$^2$) was intravenously administered while increasing the administration rate over 3 hr stepwisely (0.06 mg/m$^2$ for the first 60 min, 0.18 mg/m$^2$ for the next 60 min, and 0.36 mg/m$^2$ for the last 60 min). Serum levels of HGF were measured by ELISA. A shift of serum HGF levels on day 1 of rh-HGF administration period is shown.

In patients 1, 2, and 3, rh-HGF was administered after plasma exchange. Serum levels of HGF increased in parallel with a stepwise increase of rh-HGF dose, and reached maximum drug concentration ($C_{max}$) at the end of a 3 hr rh-HGF injection (FIG. 3). $C_{max}$ gradually increased from 18.8±6.0 ng/ml, on day 1 to 22.3±9.6 ng/ml, on day 11 during the HGF administration period (Table 2).

TABLE 2

Pharmacokinetic parameters of rh-HGF

| Parameters | Estimate values | 95% confidence interval | |
|---|---|---|---|
| Day 1 | | | |
| $C_{max}$ (ng/mL) | 18.8 | 13 | 24.7 |
| $AUC_{0-300}$ (ng/mL * min) | 1485.6 | 991.3 | 1979.8 |
| $AUC_{0-\infty}$ (ng/mL * min) | 1994 | 1214.6 | 2773.3 |
| $T_{1/2}$ (min) | 756.2 | 526.8 | 985.7 |
| CL (mL/m²/min) | 0.000361 | 0.00016 | 0.000561 |
| $V_{dss}$ (mL/m²) | 0.125 | 0.063 | 0.186 |
| Day 5 | | | |
| $C_{max}$ (ng/mL) | 21.3 | 12.8 | 29.9 |
| $AUC_{0-300}$ (ng/mL * min) | 1727.2 | 1099.7 | 2354.7 |
| $AUC_{0-\infty}$ (ng/mL * min) | 2493.8 | 1647 | 3340.5 |
| $T_{1/2}$ (min) | 843.6 | 540.5 | 1146.6 |
| CL (mL/m²/min) | 0.000277 | 0.000138 | 0.000416 |
| $V_{dss}$ (mL/m²) | 0.106 | 0.059 | 0.153 |
| Day 11 | | | |
| $C_{max}$ (ng/mL) | 22.3 | 11.4 | 33.1 |
| $AUC_{0-300}$ (ng/mL * min) | 1965.5 | 801.6 | 3129.5 |
| $AUC_{0-\infty}$ (ng/mL * min) | 3126.4 | 1355.2 | 4897.5 |
| $T_{1/2}$ (min) | 633.3 | 318 | 948.6 |
| CL (mL/m²/min) | 0.00023 | 0.000095 | 0.000365 |
| $V_{dss}$ (mL/m²) | 0.088 | 0.031 | 0.146 |

The mean value of half-life ($T_{1/2}$) of serum HGF was approximately 630 to 840 min. It has been clarified during the HGF administration period that the area under the blood concentration-time curve (AUC) gradually increased, and the clearance (CL) and steady-state volume of distribution ($V_{dss}$) gradually decreased.

(3) Drug Tolerance

Preclinical safety studies revealed that a decrease in blood pressure during rh-HGF injection and renal toxicity induced by repeated rh-HGF administration, including an increase in urinary excretion of albumin were potential adverse events in a human clinical trial. In the phase I/II study of patients with FHSA or LOHF, respiratory status was not affected by rh-HGF administration in any patient, but blood pressure decreased from mildly to moderately in approximately 1 hour after the start of HGF injection in patients 1, 2 and 3 (FIG. 4). As HGF reduces blood pressure through dilatation of capacitance vessels, the heart rate increased by up to 30%. However, this decrease in blood pressure did not require cessation of rh-HGF administration or any vasopressor therapy, and in patient 1, the blood pressure immediately recovered only with 200-300 mL infusion, and the blood pressure returned to resting levels after the completion of HGF administration. Prior infusion ameliorated HGF-induced blood pressure reduction, as observed in preclinical animal experiments (FIG. 1C). In any event, the decrease in blood pressure observed during HGF injection was reversible, and did not affect patients' general condition. Although patients 2 and 3 also exhibited, though patient 4 did not, blood pressure reduction during rh-HGF injection, their general conditions were stable even without giving additional infusion or ceasing the rh-HGF administration. Patient 2, who awoke from hepatic encephalopathy on day 3 of the HGF administration period, did not suffer from any symptoms during HGF administration, even though the heart rate increased by up to about 30% (FIG. 4).

All patients showed slight to mild increase in urinary excretion of albumin at enrollment and a decrease in urine volume during the study period. However, repeated administration of rh-HGF did not increase urinary excretion of albumin. In addition, urine volume was affected by several factors other than rh-HGF administration, including volume of infusion, amount of circulating plasma, and diuretic administration. Although hypokalemia, anemia, a decrease in platelet count, prolonged PT, a decrease in anti-thrombin III, and hematuria were also observed in three of four patients, there was no apparent evidence for a causal relationship between these adverse events and rh-HGF administration. Patient 3, who died of advanced hepatic failure during the observation period, exhibited respiratory failure. However, this severe adverse event was associated with progression of hepatic failure, not rh-HGF. No other severe adverse events directly caused by single or repeated administration of rh-HGF were observed during the study period. Of particular importance, patient 2, who had awakened from hepatic encephalopathy, showed no symptom or sign during rh-HGF administration. Therefore, we concluded that rh-HGF administered intravenously with a stepwise increase for up to 14 consecutive days was very well tolerated.

(4) Shift of Hepatic Encephalopathy and Various Evaluation Parameters During Study Period Three out of four patients exhibited hepatic encephalopathy at enrollment (Table 1). Patient 1 presented with grade II hepatic encephalopathy at the beginning of protocol therapy. This patient did not recover from hepatic encephalopathy either during or after the study period. The patient ultimately died 68 days after the onset of hepatic encephalopathy (FIG. 7-1). In patient 2, who had FHSA and ultimately survived, plasma exchange was performed on days 2, 4, and 8 during the HGF administration period, and hepatic encephalopathy had improved by day 3 (FIG. 7-2). Patient 3 showed advanced hepatic encephalopathy at enrollment. Although the consciousness level was transiently alleviated during the rh-HGF administration period, hepatic encephalopathy continued to progress during the observation period, and the patient died 28 days after the onset of hepatic encephalopathy (FIG. 7-3). Patient 4 had already recovered from hepatic encephalopathy at enrollment, and did not show any reduction of consciousness level during the study period (FIG. 7-4).

Figure 5:
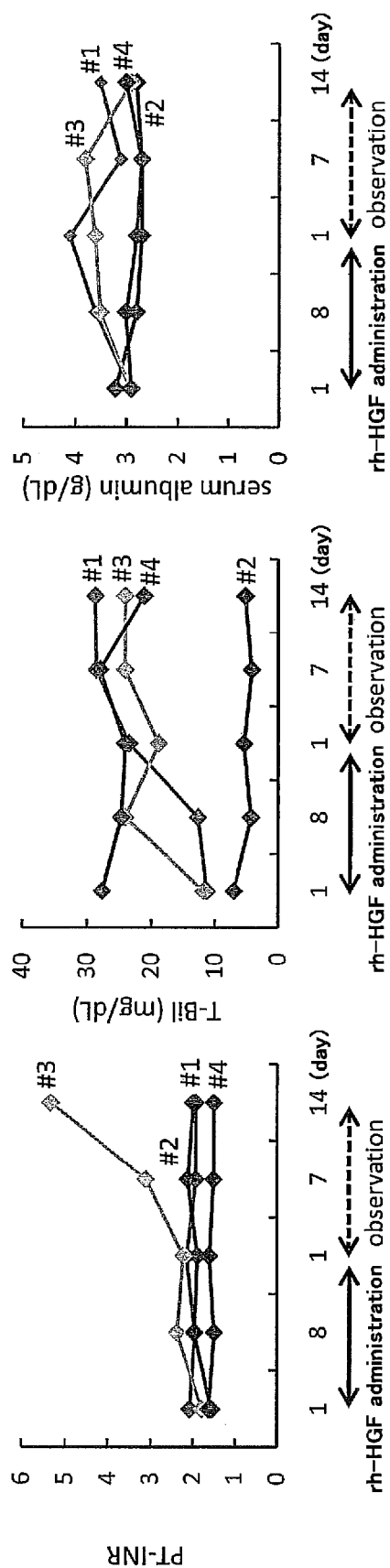
FIG. 5 shows changes in test data results during rh-HGF administration and observation period. Prothrombin time-international normalized ratio (PT-INR), total bilirubin (T-Bil) and serum albumin were measured before rh-HGF administration (day 1 of rh-HGF administration period), on day 7 of the rh-HGF administration period, and 1, 7 and 14 days after the administration.

Prothrombin time-international normalized ratio (PT-INR), total bilirubin (T-Bil) and serum albumin were not affected during the rh-HGF administration and observation period (FIG. 5).

Then, the effect of administration of rh-HGF on patient survival was evaluated. In a nationwide survey of the patients with FH or LOHF (1998-2002) in Japan, the survival rate of the patients (n=192) who met this study's inclusion criteria was only 17.7% (n=34), and 71% (n=135) of the patients (n=190) who did not recover from FHSA and LOHF died within 28 days following the onset of hepatic encephalopathy. In contrast, in this clinical test, 3 out of 4 cases (75%) survived during the study period, and 2 cases (50%) were finally saved. The results strongly suggest that HGF can be an effective treatment means for FH or LOHF patients who cannot undergo liver transplantation.

The dose and/or administration period of rh-HGF used in this study might have been too low to produce a more beneficial effect. While the dose chosen for this study is based on a scaling of the doses used in pre-clinical animal studies, and has safety ensured in several repeated administration toxicity tests, the results of the animal experiment show that at least 4-fold dose increase is possible. Also, this dose, corresponding to 0.1 mg/kg in rodents, has been reported to promote liver regeneration in normal and partially hepatectomized rats [Ishii, T. et al., J. Biochem., 1995; 117:1105-1112], though it does not guarantee effectiveness when severe liver injury is accompanied. The treatment duration is based on a nationwide survey of FH and LOHF in Japan between 1998 and 2002. In this survey, 90.4% (n=47) of recovering patients from FHSA and LOHF (n=52) awaked within 14 days after hepatic encephalopathy occurred, and 71% (n=135) of non-recovering patients (n=190) died within 28 days following the onset of hepatic encephalopathy. Based on the above findings, rh-HGF administration for 14 days with subsequent 14-day follow-up, was considered to be sufficient to evaluate safety and efficacy. In severe acute liver failure such as FH and LOHF, the dose of rh-HGF adopted in this study was suggested to be insufficient for inducing liver regeneration and suppressing liver injury, or the administration period of 14 days may be short in some cases.

(5) Shift of Serum AFP and Soluble Fas Value During Study Period

Patients 1-4 were monitored for serum α-fetoprotein (AFP) and soluble Fas value during the study period. In each case, blood samples were collected in the early mornings of before rh-HGF administration (day 1), day 3 of administration, day 5 of administration, day 8 of administration, the next day of the completion of the administration (day 1), day 7 from the completion of the administration and day 14 from the completion of the administration, and the serum AFP value was measured by a chemiluminescent enzyme immunoassay (CLEIA) method. The alanine transaminase (ALT) level of each serum sample was also measured. In addition, the serum soluble Fas value was measured before rh-HGF administration and the next day of the completion of the administration. Furthermore, the liver volume was measured by abdominal computed tomography (CT) before rh-human HGF administration, immediately after the completion of the administration and day 14 from the completion of the administration.

Figure 6:
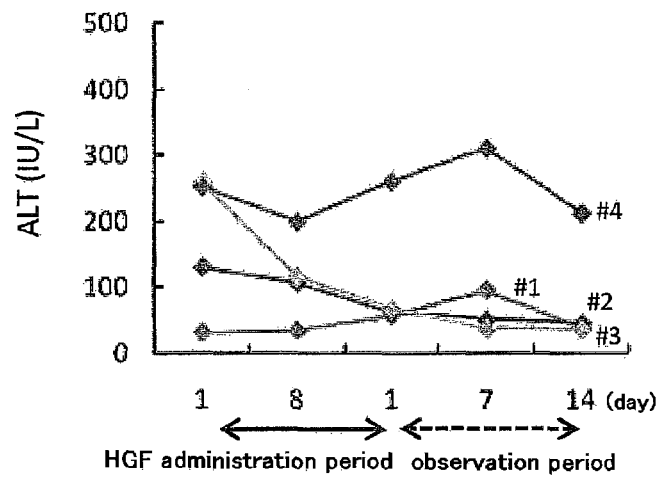
FIG. 6 shows time-course changes of alanine transaminase (ALT) and serum α-fetoprotein (AFP) during rh-HGF administration and observation period, and of serum soluble Fas before rh-HGF administration and after completion of the administration period.
Figure 6:
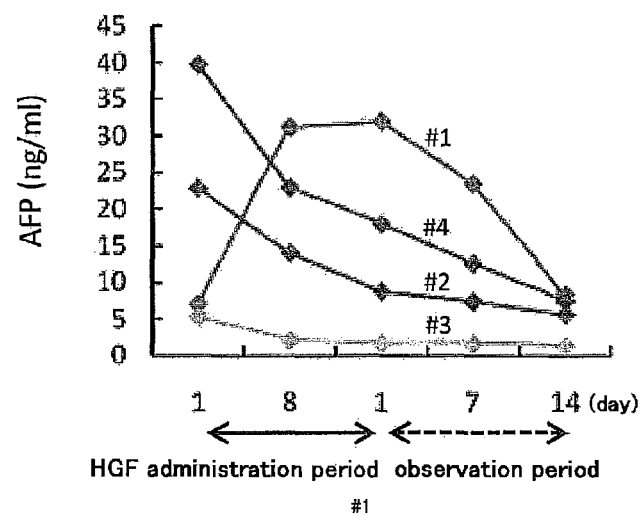
Figure 6:
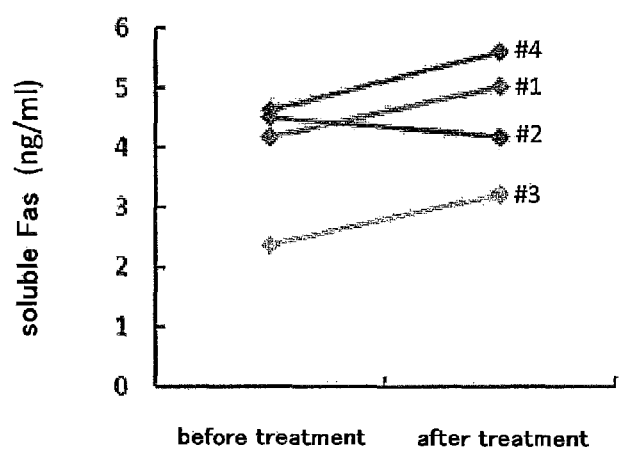

The serum AFP values before administration, day 8 of administration, the next day of the completion of the administration, day 7 from the completion of the administration and day 14 from the completion of the administration were plotted in FIG. 6. In patient 1, the serum AFP value was 7.0 ng/mL and within the standard value (not more than 10.0 ng/mL) before rh-HGF administration, but increased to 15.0 ng/mL on day 3 of rh-HGF administration, and reached 38.9 ng/mL on day 11 of administration. It mildly decreased to 32 ng/mL on the next day of the completion of the administration, thereafter further decreased to 23.5 ng/mL on day 7 from the completion of the administration, and was 8.3 ng/mL and within the standard value on day 14 from the completion of the administration. Since the serum AFP value rapidly increased during the rh-HGF administration and decreased after the completion of the administration as mentioned above, serum AFP value was considered to be a biomarker for examining the efficacy of HGF, i.e., liver regeneration promoting action of HGF. On the other hand, in patient 3, the serum AFP value was within the standard value from before the rh-HGF administration throughout the study period, and liver regeneration induction is considered to have been absent even by rh-HGF administration. While both patients 1 and 3 were fatal cases, the clinical progression was vastly different. In patient 1, the disease state did not progress and the general condition was stable in the rh-HGF administration period (13 days) and the observation period (14 days) thereafter, and the survival period was prolonged since the period from the onset to death was 79 days (period from encephalopathy development to death was 68 days). In contrast, patient 3 was an extremely severe case, and the patient died on day 13 of the observation period after 11 days of rh-HGF administration. That is, in patient 1, liver regeneration was induced by rh-HGF administration to show a life-prolonging effect; however, in patient 3, it is considered that liver regeneration was not induced. In both patients 2 and 4, serum AFP mildly increased before rh-HGF administration, and liver regeneration is presumed to have already been induced slightly. Since these patients were under medication with prednisolone (PSL) in parallel to rh-HGF (FIGS. 7-2 and 7-4), it is considered that liver regeneration was induced in all cases but serum AFP gradually decreased since PSL influenced AFP expression. In fact, abdominoscopy and liver biopsy in patient 2 about 3 months after the rh-HGF administration showed images of liver regeneration.

The liver volume (patient 1) conventionally said to be able to be an index of liver regeneration induction is 1055 mL before rh-HGF administration, 1076 mL on the next day of the completion of the administration, and 984 mL on day 14 from the completion of the administration. Thus, not much difference was found during the rh-HGF administration, and the volume mildly decreased after the completion of the administration (Table 3). The serum albumin value did not change much in all patients 1-4 during the rh-HGF administration (FIG. 5). Therefore, it was shown that AFP can be an index (biomarker) of liver regenerative effect, which is superior to liver volume and serum albumin.

TABLE 3

| recombinant human HGF | before administration | immediately after administration | day 14 from administration |
|---|---|---|---|
| liver volume (mL) | 1055 | 1076 | 984 |

On the other hand, the serum soluble Fas value showed an increase before and after the administration of rh-HGF in patients 1, 3 and 4, but a significant change was not found in patient 2 (FIG. 6). In patient 1, ALT, which is considered a serum marker of hepatocellular injury, showed a comparatively low value, but mildly increased after the completion of the rh-HGF administration. This may be because the apoptosis suppression by the HGF treatment stopped on completion of the administration, and mild hepatocellular injury was induced. In patient 1, an anti-apoptotic effect was also induced besides induction of the liver regeneration, and these are considered to have contributed to the prolongation of the survival period. On the other hand, in patient 3, soluble Fas increased by rh-HGF administration but the values before and after the administration were low as compared to those in other 3 cases (FIG. 6), which suggests a possibility that the anti-apoptotic action of rh-HGF was not exerted sufficiently enough to exceed the extremely severe liver injury in this case. The decrease in the serum ALT value during the administration period (FIG. 6) also supports induction of an anti-apoptotic effect of rh-HGF administration in this case.

In patient 2, steroid administration improved the serum ALT value. In patient 4, however, serum ALT value was higher (stronger hepatocellular injury), and steroid administration scarcely improved the serum ALT value. In both cases, soluble Fas before rh-HGF administration was of the same level and, if it increases in compensation for hepatocellular injury (as a biological reaction to protect hepatocyte), a possibility is suggested that an anti-apoptotic action (increase in soluble Fas) by rh-HGF was not necessary in patient 2 where serum ALT value decreased by steroid administration (hepatocellular injury was suppressed), whereas in patient 4, since hepatocellular injury (serum ALT increase) was persistent, induction of soluble Fas by rh-HGF in addition to the compensatory increase in soluble Fas suppressed apoptosis, which finally led to the survival.

From the foregoing, it is shown that AFP and soluble Fas are available as biomarkers for the liver regeneration promoting action and anti-apoptotic action of HGF, and whether the effect of both or either one of the liver regeneration induction and apoptosis suppression is induced by the administration of HGF in a patient with liver injury can be judged by measuring the changes in the level of the both markers before and after administration of HGF in the patient, and comparing them in combination (in combination with other biomarkers such as ALT value and the like as necessary) with the clinical progress of the patient.

Industrial Applicability

According to the present invention, since lifesaving even in acute liver failure with the progression of hepatic encephalopathy such as fulminant hepatitis, late onset hepatic failure and the like is possible while ensuring the reversibility of side effects, administration of an HGF preparation at a stage of acute liver failure without hepatic coma with lower severity prevents progression into fulminant hepatitis and late onset hepatic failure even in patients unacceptable for liver transplantation and can strikingly increase the lifesaving rate. Moreover, a combined use of the two efficacy biomarkers of HGF in the present invention is extremely useful since it enables stratification of hepatic failure patients, determination of the optimal HGF dose and/or administration period for each patient group, and provision of a safer HGF treatment with a high treatment effect.

This application is based on a patent application No. 2011-92516 (filing date: Apr. 18, 2011), the contents of which are incorporated in full herein by reference.

The invention claimed is:

1. A method of treating acute liver failure comprising administering an effective amount of a hepatocyte growth factor having an amino acid sequence with not less than 98% identity to the amino acid sequence of amino acids 32-728 of SEQ ID NO: 2 to a patient in need thereof, wherein the hepatocyte growth factor is administered by once daily intravenous infusion and about 10% of the one dose is administered in the first ⅓ of the single administration time, about 30% of the one dose is administered in the next ⅓ of the single administration time, and about 60% of the one dose is administered in the final ⅓ of the single administration time, and wherein patient survival is prolonged.

2. The method of claim 1, wherein the hepatocyte growth factor is a human hepatocyte growth factor having the amino acid sequence of amino acids 30-728 or amino acids 32-728 of SEQ ID NO: 2, or a natural allele variant or polymorphic variant thereof.

3. The method of claim 1, wherein the hepatocyte growth factor is a human hepatocyte growth factor having the amino acid sequence of amino acids 30-728 or amino acids 32-728 of SEQ ID NO: 2.

4. The method of claim 1, wherein the hepatocyte growth factor is administered by once daily intravenous infusion over 2-6 hours.

5. The method of claim 4, wherein the hepatocyte growth factor is a human hepatocyte growth factor having the amino acid sequence of amino acids 30-728 or amino acids 32-728 of SEQ ID NO: 2, or a natural allele variant or polymorphic variant thereof.

6. The method of claim 4, wherein the hepatocyte growth factor is a human hepatocyte growth factor having the amino acid sequence of amino acids 30-728 or amino acids 32-728 of SEQ ID NO: 2.

7. The method of claim 1, wherein the patient has fulminant hepatitis or late onset hepatic failure.

8. The method of claim 7, wherein the hepatocyte growth factor is a human hepatocyte growth factor having the amino acid sequence of amino acids 30-728 or amino acids 32-728 of SEQ ID NO: 2, or a natural allele variant or polymorphic variant thereof.

9. The method of claim 7, wherein the hepatocyte growth factor is a human hepatocyte growth factor having the amino acid sequence of amino acids 30-728 or amino acids 32-728 of SEQ ID NO: 2.

10. The method of claim 7, wherein the hepatocyte growth factor is administered by once daily intravenous infusion over 2-6 hours.

11. The method of claim 10, wherein the hepatocyte growth factor is a human hepatocyte growth factor having the amino acid sequence of amino acids 30-728 or amino acids 32-728 of SEQ ID NO: 2, or a natural allele variant or polymorphic variant thereof.

12. The method of claim 10, wherein the hepatocyte growth factor is a human hepatocyte growth factor having the amino acid sequence of amino acids 30-728 or amino acids 32-728 of SEQ ID NO: 2.

\* \* \* \* \*

SEQUENCE LISTING

```
<160> NUMBER OF SEQ ID NOS: 2

<210> SEQ ID NO 1
<211> LENGTH: 2187
<212> TYPE: DNA
<213> ORGANISM: Homo sapiens
<220> FEATURE:
<221> NAME/KEY: CDS
<222> LOCATION: (1)..(2187)
<220> FEATURE:
<221> NAME/KEY: sig_peptide
<222> LOCATION: (1)..(87)
<220> FEATURE:
<221> NAME/KEY: sig_peptide
<222> LOCATION: (1)..(93)

<400> SEQUENCE: 1 atg tgg gtg acc aaa ctc ctg cca gcc ctg ctg ctg cag cat gtc ctc        48
Met Trp Val Thr Lys Leu Leu Pro Ala Leu Leu Leu Gln His Val Leu
1               5                   10                  15 ctg cat ctc ctc ctg ctc ccc atc gcc atc ccc tat gca gag gga caa        96
Leu His Leu Leu Leu Leu Pro Ile Ala Ile Pro Tyr Ala Glu Gly Gln
            20                  25                  30 agg aaa aga aga aat aca att cat gaa ttc aaa aaa tca gca aag act       144
Arg Lys Arg Arg Asn Thr Ile His Glu Phe Lys Lys Ser Ala Lys Thr
        35                  40                  45 acc cta atc aaa ata gat cca gca ctg aag ata aaa acc aaa aaa gtg       192
Thr Leu Ile Lys Ile Asp Pro Ala Leu Lys Ile Lys Thr Lys Lys Val
    50                  55                  60 aat act gca gac caa tgt gct aat aga tgt act agg aat aaa gga ctt       240
Asn Thr Ala Asp Gln Cys Ala Asn Arg Cys Thr Arg Asn Lys Gly Leu
65                  70                  75                  80 cca ttc act tgc aag gct ttt gtt ttt gat aaa gca aga aaa caa tgc       288
Pro Phe Thr Cys Lys Ala Phe Val Phe Asp Lys Ala Arg Lys Gln Cys
                85                  90                  95 ctc tgg ttc ccc ttc aat agc atg tca agt gga gtg aaa aaa gaa ttt       336
Leu Trp Phe Pro Phe Asn Ser Met Ser Ser Gly Val Lys Lys Glu Phe
            100                 105                 110 ggc cat gaa ttt gac ctc tat gaa aac aaa gac tac att aga aac tgc       384
Gly His Glu Phe Asp Leu Tyr Glu Asn Lys Asp Tyr Ile Arg Asn Cys
        115                 120                 125 atc att ggt aaa gga cgc agc tac aag gga aca gta tct atc act aag       432
Ile Ile Gly Lys Gly Arg Ser Tyr Lys Gly Thr Val Ser Ile Thr Lys
    130                 135                 140
```

-continued

| | | |
|---|---|---|
| agt ggc atc aaa tgt cag ccc tgg agt tcc atg ata cca cac gaa cac<br>Ser Gly Ile Lys Cys Gln Pro Trp Ser Ser Met Ile Pro His Glu His<br>145                              150                        155                          160 | | 480 |
| agc ttt ttg cct tcg agc tat cgg ggt aaa gac cta cag gaa aac tac<br>Ser Phe Leu Pro Ser Ser Tyr Arg Gly Lys Asp Leu Gln Glu Asn Tyr<br>                            165                        170                        175 | | 528 |
| tgt cga aat cct cga ggg gaa gaa ggg gga ccc tgg tgt ttc aca agc<br>Cys Arg Asn Pro Arg Gly Glu Glu Gly Gly Pro Trp Cys Phe Thr Ser<br>                            180                        185                        190 | | 576 |
| aat cca gag gta cgc tac gaa gtc tgt gac att cct cag tgt tca gaa<br>Asn Pro Glu Val Arg Tyr Glu Val Cys Asp Ile Pro Gln Cys Ser Glu<br>195                              200                        205 | | 624 |
| gtt gaa tgc atg acc tgc aat ggg gag agt tat cga ggt ctc atg gat<br>Val Glu Cys Met Thr Cys Asn Gly Glu Ser Tyr Arg Gly Leu Met Asp<br>          210                        215                        220 | | 672 |
| cat aca gaa tca ggc aag att tgt cag cgc tgg gat cat cag aca cca<br>His Thr Glu Ser Gly Lys Ile Cys Gln Arg Trp Asp His Gln Thr Pro<br>225                              230                        235                        240 | | 720 |
| cac cgg cac aaa ttc ttg cct gaa aga tat ccc gac aag ggc ttt gat<br>His Arg His Lys Phe Leu Pro Glu Arg Tyr Pro Asp Lys Gly Phe Asp<br>                            245                        250                        255 | | 768 |
| gat aat tat tgc cgc aat ccc gat ggc cag ccg agg cca tgg tgc tat<br>Asp Asn Tyr Cys Arg Asn Pro Asp Gly Gln Pro Arg Pro Trp Cys Tyr<br>                            260                        265                        270 | | 816 |
| act ctt gac cct cac acc cgc tgg gag tac tgt gca att aaa aca tgc<br>Thr Leu Asp Pro His Thr Arg Trp Glu Tyr Cys Ala Ile Lys Thr Cys<br>                        275                        280                        285 | | 864 |
| gct gac aat act atg aat gac act gat gtt cct ttg gaa aca act gaa<br>Ala Asp Asn Thr Met Asn Asp Thr Asp Val Pro Leu Glu Thr Thr Glu<br>290                              295                        300 | | 912 |
| tgc atc caa ggt caa gga gaa ggc tac agg ggc act gtc aat acc att<br>Cys Ile Gln Gly Gln Gly Glu Gly Tyr Arg Gly Thr Val Asn Thr Ile<br>305                              310                        315                        320 | | 960 |
| tgg aat gga att cca tgt cag cgt tgg gat tct cag tat cct cac gag<br>Trp Asn Gly Ile Pro Cys Gln Arg Trp Asp Ser Gln Tyr Pro His Glu<br>                            325                        330                        335 | | 1008 |
| cat gac atg act cct gaa aat ttc aag tgc aag gac cta cga gaa aat<br>His Asp Met Thr Pro Glu Asn Phe Lys Cys Lys Asp Leu Arg Glu Asn<br>                            340                        345                        350 | | 1056 |
| tac tgc cga aat cca gat ggg tct gaa tca ccc tgg tgt ttt acc act<br>Tyr Cys Arg Asn Pro Asp Gly Ser Glu Ser Pro Trp Cys Phe Thr Thr<br>                            355                        360                        365 | | 1104 |
| gat cca aac atc cga gtt ggc tac tgc tcc caa att cca aac tgt gat<br>Asp Pro Asn Ile Arg Val Gly Tyr Cys Ser Gln Ile Pro Asn Cys Asp<br>370                              375                        380 | | 1152 |
| atg tca cat gga caa gat tgt tat cgt ggg aat ggc aaa aat tat atg<br>Met Ser His Gly Gln Asp Cys Tyr Arg Gly Asn Gly Lys Asn Tyr Met<br>385                              390                        395                        400 | | 1200 |
| ggc aac tta tcc caa aca aga tct gga cta aca tgt tca atg tgg gac<br>Gly Asn Leu Ser Gln Thr Arg Ser Gly Leu Thr Cys Ser Met Trp Asp<br>                            405                        410                        415 | | 1248 |
| aag aac atg gaa gac tta cat cgt cat atc ttc tgg gaa cca gat gca<br>Lys Asn Met Glu Asp Leu His Arg His Ile Phe Trp Glu Pro Asp Ala<br>                        420                        425                        430 | | 1296 |
| agt aag ctg aat gag aat tac tgc cga aat cca gat gat gat gct cat<br>Ser Lys Leu Asn Glu Asn Tyr Cys Arg Asn Pro Asp Asp Asp Ala His<br>          435                        440                        445 | | 1344 |
| gga ccc tgg tgc tac acg gga aat cca ctc att cct tgg gat tat tgc<br>Gly Pro Trp Cys Tyr Thr Gly Asn Pro Leu Ile Pro Trp Asp Tyr Cys<br>450                              455                        460 | | 1392 |

```
cct att tct cgt tgt gaa ggt gat acc aca cct aca ata gtc aat tta    1440
Pro Ile Ser Arg Cys Glu Gly Asp Thr Thr Pro Thr Ile Val Asn Leu
465                 470                 475                 480 gac cat ccc gta ata tct tgt gcc aaa acg aaa caa ttg cga gtt gta    1488
Asp His Pro Val Ile Ser Cys Ala Lys Thr Lys Gln Leu Arg Val Val
                485                 490                 495 aat ggg att cca aca cga aca aac ata gga tgg atg gtt agt ttg aga    1536
Asn Gly Ile Pro Thr Arg Thr Asn Ile Gly Trp Met Val Ser Leu Arg
        500                 505                 510 tac aga aat aaa cat atc tgc gga gga tca ttg ata aag gag agt tgg    1584
Tyr Arg Asn Lys His Ile Cys Gly Gly Ser Leu Ile Lys Glu Ser Trp
    515                 520                 525 gtt ctt act gca cga cag tgt ttc cct tct cga gac ttg aaa gat tat    1632
Val Leu Thr Ala Arg Gln Cys Phe Pro Ser Arg Asp Leu Lys Asp Tyr
530                 535                 540 gaa gct tgg ctt gga att cat gat gtc cac gga aga gga gat gag aaa    1680
Glu Ala Trp Leu Gly Ile His Asp Val His Gly Arg Gly Asp Glu Lys
545                 550                 555                 560 tgc aaa cag gtt ctc aat gtt tcc cag ctg gta tat ggc cct gaa gga    1728
Cys Lys Gln Val Leu Asn Val Ser Gln Leu Val Tyr Gly Pro Glu Gly
                565                 570                 575 tca gat ctg gtt tta atg aag ctt gcc agg cct gct gtc ctg gat gat    1776
Ser Asp Leu Val Leu Met Lys Leu Ala Arg Pro Ala Val Leu Asp Asp
        580                 585                 590 ttt gtt agt acg att gat tta cct aat tat gga tgc aca att cct gaa    1824
Phe Val Ser Thr Ile Asp Leu Pro Asn Tyr Gly Cys Thr Ile Pro Glu
    595                 600                 605 aag acc agt tgc agt gtt tat ggc tgg ggc tac act gga ttg atc aac    1872
Lys Thr Ser Cys Ser Val Tyr Gly Trp Gly Tyr Thr Gly Leu Ile Asn
610                 615                 620 tat gat ggc cta tta cga gtg gca cat ctc tat ata atg gga aat gag    1920
Tyr Asp Gly Leu Leu Arg Val Ala His Leu Tyr Ile Met Gly Asn Glu
625                 630                 635                 640 aaa tgc agc cag cat cat cga ggg aag gtg act ctg aat gag tct gaa    1968
Lys Cys Ser Gln His His Arg Gly Lys Val Thr Leu Asn Glu Ser Glu
                645                 650                 655 ata tgt gct ggg gct gaa aag att gga tca gga cca tgt gag ggg gat    2016
Ile Cys Ala Gly Ala Glu Lys Ile Gly Ser Gly Pro Cys Glu Gly Asp
        660                 665                 670 tat ggt ggc cca ctt gtt tgt gag caa cat aaa atg aga atg gtt ctt    2064
Tyr Gly Gly Pro Leu Val Cys Glu Gln His Lys Met Arg Met Val Leu
    675                 680                 685 ggt gtc att gtt cct ggt cgt gga tgt gcc att cca aat cgt cct ggt    2112
Gly Val Ile Val Pro Gly Arg Gly Cys Ala Ile Pro Asn Arg Pro Gly
690                 695                 700 att ttt gtc cga gta gca tat tat gca aaa tgg ata cac aaa att att    2160
Ile Phe Val Arg Val Ala Tyr Tyr Ala Lys Trp Ile His Lys Ile Ile
705                 710                 715                 720 tta aca tat aag gta cca cag tca tag                                2187
Leu Thr Tyr Lys Val Pro Gln Ser
                725
```

<210> SEQ ID NO 2
<211> LENGTH: 728
<212> TYPE: PRT
<213> ORGANISM: Homo sapiens

<400> SEQUENCE: 2

```
Met Trp Val Thr Lys Leu Leu Pro Ala Leu Leu Leu Gln His Val Leu
1               5                   10                  15
```

```
Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430
```

```
Ser Lys Leu Asn Glu Asn Tyr Cys Arg Asn Pro Asp Asp Ala His
        435                 440                 445
Gly Pro Trp Cys Tyr Thr Gly Asn Pro Leu Ile Pro Trp Asp Tyr Cys
    450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
                500                 505                 510
Tyr Arg Asn Lys His Ile Cys Gly Gly Ser Leu Ile Lys Glu Ser Trp
            515                 520                 525
Val Leu Thr Ala Arg Gln Cys Phe Pro Ser Arg Asp Leu Lys Asp Tyr
    530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
                580                 585                 590
Phe Val Ser Thr Ile Asp Leu Pro Asn Tyr Gly Cys Thr Ile Pro Glu
            595                 600                 605
Lys Thr Ser Cys Ser Val Tyr Gly Trp Gly Tyr Thr Gly Leu Ile Asn
        610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
                660                 665                 670
Tyr Gly Gly Pro Leu Val Cys Glu Gln His Lys Met Arg Met Val Leu
        675                 680                 685
Gly Val Ile Val Pro Gly Arg Gly Cys Ala Ile Pro Asn Arg Pro Gly
    690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725
```